United States Patent
Gronemeyer et al.

(10) Patent No.: US 8,338,473 B2
(45) Date of Patent: Dec. 25, 2012

(54) DERIVATIVES OF PSAMMAPLIN A, A METHOD FOR THEIR SYNTHESIS AND THEIR USES FOR THE PREVENTION OR TREATMENT OF CANCER

(75) Inventors: Hinrich Gronemeyer, Oberkirch (DE); Lucia Altucci, Naples (IT); Angel De Lera, Vigo (ES); Hendrik Gerard Stunnenberg, Nijmegen (NL)

(73) Assignees: Centre National de la Recherche Scientifique, Paris (FR); Universite de Strasbourg, Strasbourg Cedex (FR); Institut National de la Sante et de la Recherche Medicale (Inserm), Paris (FR); Universidade de Vito, CP Vigo (ES); Seconda Universita Degli Studi di Napoli, Caserta (IT); Radboud University Nijmegen, Ex Nijmegen (NL)

( * ) Notice: Subject to any disclaimer, the term of this patent is extended or adjusted under 35 U.S.C. 154(b) by 275 days.

(21) Appl. No.: 12/528,020

(22) PCT Filed: Feb. 28, 2008

(86) PCT No.: PCT/IB2008/001887
§ 371 (c)(1),
(2), (4) Date: Feb. 1, 2010

(87) PCT Pub. No.: WO2008/125988
PCT Pub. Date: Oct. 23, 2008

(65) Prior Publication Data
US 2010/0120885 A1 May 13, 2010

(30) Foreign Application Priority Data

Feb. 28, 2007 (EP) .................... 07290253

(51) Int. Cl.
*A61K 31/404* (2006.01)
*C07D 209/12* (2006.01)
(52) U.S. Cl. ......... 514/414; 514/419; 548/455; 548/495
(58) Field of Classification Search .............. None
See application file for complete search history.

(56) References Cited

U.S. PATENT DOCUMENTS
5,607,934 A * 3/1997 Tone et al. ............... 514/254.09

FOREIGN PATENT DOCUMENTS
EP         0 501 378        2/1992
WO     WO 2007/025169        3/2007

OTHER PUBLICATIONS

Golub et al. "Molecular Classification of Cancer: Class Discovery and Class Prediction by Gene Expression Monitoring." Science (1999), vol. 286, 521-537.*
Lala et al. "Role of nitric oxide in tumor progression: Lessons from experimental tumors." Cancer and Metastasis Reviews (1998), 17(1), 91-106.*
"cancer." MedLine Plus. (2009). Accessed Mar. 17, 2009. <http://www.nlm.nih.gov/medlineplus/cancer.html>.*
Nebbioso et al., "Death Receptor Pathway Activation and Increase of ROS Production by the Triple Epigenetic Inhibitor UV15008", Molecular Cancer Therapeutics, 10:2394-2404 (Oct. 6, 2011).
Hahn et al., "Rules for Making Human Tumor Cells", N Engl J Med, 347(20):1593-1603 (Nov. 14, 2002).
Hahn et al., "Creation of human tumour cells with defined genetic elements", Nature, 400:464-468 (Jul. 29, 1999).

* cited by examiner

*Primary Examiner* — Joseph K. McKane
*Assistant Examiner* — Alicia L Otton
(74) *Attorney, Agent, or Firm* — Morgan, Lewis & Bockius LLP

(57) ABSTRACT

Derivatives of psammaplin A responding to formula (I), a method for their synthesis and their use for the preparation of a medicament for preventing and for treating a tumor or a cancer. Formula (I).

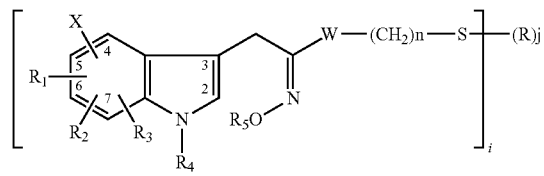

17 Claims, 16 Drawing Sheets a

Proliferation b

Apoptosis

A-375 cell line

SAHA

MS-275

UVI 5008

HCT-116 cell line

SAHA

MS-275

UVI 5008

DU-145 cell line

SAHA

MS-275

UVI 5008

Figure 1:
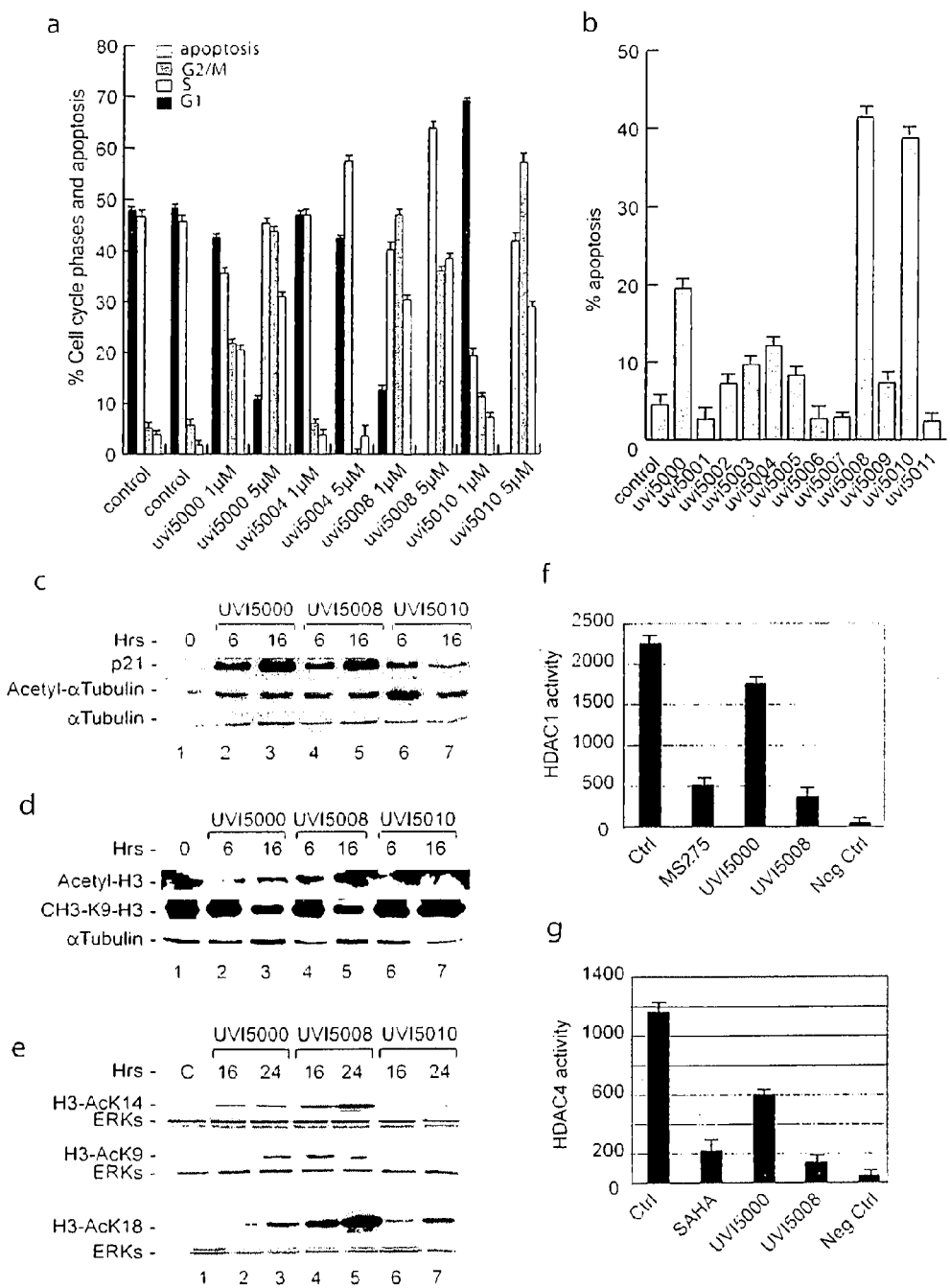

| # | b | $b^{++}$ | $b^*$ | $b^{*++}$ | $b^0$ | $b^{0++}$ | Seq. | y | $y^{++}$ | $y^*$ | $y^{*++}$ | $y^0$ | $y^{0++}$ | # |
|---|---|---|---|---|---|---|---|---|---|---|---|---|---|---|
| 1 | 164.0706 | 82.5389 | | | | | Y | | | | | | | 10 |
| 2 | 292.1292 | 146.5682 | 275.1026 | 138.0550 | | | Q | 1129.6575 | 565.3324 | 1112.6310 | 556.8191 | 1111.6470 | 556.3271 | 9 |
| 3 | 462.2347 | 231.6210 | 445.2082 | 223.1077 | | | K | 1001.5990 | 501.3031 | 984.5724 | 492.7898 | 983.5884 | 492.2978 | 8 |
| 4 | 549.2668 | 275.1370 | 532.2402 | 266.6237 | 531.2562 | 266.1317 | S | 831.4934 | 416.2504 | 814.4669 | 407.7371 | 813.4829 | 407.2451 | 7 |
| 5 | 650.3144 | 325.6609 | 633.2879 | 317.1476 | 632.3039 | 316.6556 | T | 744.4614 | 372.7343 | 727.4349 | 364.2211 | 726.4508 | 363.7291 | 6 |
| 6 | 779.3570 | 390.1821 | 762.3305 | 381.6689 | 761.3465 | 381.1769 | E | 643.4137 | 322.2105 | 626.3872 | 313.6972 | 625.4032 | 313.2052 | 5 |
| 7 | 892.4411 | 446.7242 | 875.4145 | 438.2109 | 874.4305 | 437.7189 | L | 514.3711 | 257.6892 | 497.3446 | 249.1759 | | | 4 |
| 8 | 1005.5251 | 503.2662 | 988.4986 | 494.7529 | 987.5146 | 494.2609 | L | 401.2871 | 201.1472 | 384.2605 | 192.6339 | | | 3 |
| 9 | 1118.6092 | 559.8082 | 1101.5827 | 551.2950 | 1100.5986 | 550.8030 | I | 288.2030 | 144.6051 | 271.1765 | 136.0919 | | | 2 |
| 10 | | | | | | | R | 175.1190 | 88.0631 | 158.0924 | 79.5498 | | | 1 |

FIGURE 10B

DERIVATIVES OF PSAMMAPLIN A, A METHOD FOR THEIR SYNTHESIS AND THEIR USES FOR THE PREVENTION OR TREATMENT OF CANCER

CROSS-REFERENCE TO RELATED APPLICATIONS

The present application is a U.S. National Phase Application of International Application PCT/IB2008/001887, filed on Feb. 28, 2008, which claims the benefit of an European Patent Application No. 07290253.9, filed on Feb. 28, 2007, all of which are herein incorporated by reference in their entirety.

The invention is related to novel derivatives of psammaplin A, a method for their synthesis and their use for the prevention and/or the treatment of a cancer or a tumour.

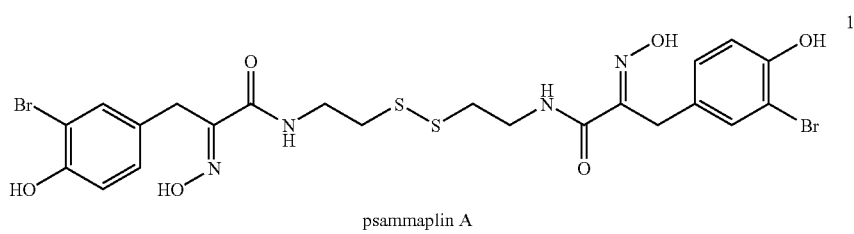

psammaplin A

Psammaplin A (1) is a symmetrical bromotyrosine-derived disulfide dimer that was originally isolated in 1987 from an unidentified sponge (Arabshahi, L.; Schmitz, F. J. *J Org. Chem.* 1987, 52, 3584-3586), *Thorectopsamma xana* (Rodriguez, A. D. et al., *Tetrahedron Lett.* 1987, 28, 4989-4992) and *Psammaplysilla* sp (Quinñoá, E.; Crews, P. *Tetrahedron Lett.* 1987, 28, 3229-3232). Early studies revealed that psammaplin A had general antibacterial and antitumor properties. In 1999, it was found that psammaplin A exhibited significant in vitro antibacterial activity against both *Staphylococcus aureus* (SA) and methicillin-resistant *Staphylococcus aureus* (MRSA), which was inferred to be the result of induced bacterial DNA synthesis arrest by psammaplin A through inhibition of DNA gyrase (Kim, D. et al., *Arch. Pharm. Res.* 1999, 22, 25-29). Additionally, psammaplin A has been reported to exhibit certain inhibition of a number of enzymes including topoisomerase II (topo II) (Kim, D. et al., *Anticancer Res.* 1999, 19, 4085-4090), farnesyl protein transferase and leucine aminopeptidase (Shin, J. et al., J. *Tetrahedron* 2000, 56, 9071-9077), and chitinase, as recently reported (Tabudravu, J. N. et al., *Bioorg. Med. Chem* 2002, 10, 1123-1128). Among these enzymes, topo II, required for eukaryotic DNA replication, as well as bacterial DNA gyrase, belong to the topoisomerase family of enzymes responsible for the remodeling of DNA topology. It was recently reported that psammaplin A displayed significant cytotoxicity against human lung (A549), ovarian (SKOV-3), skin (SK-MEL-2), CNS (XF498), and colon (HCT15) cancer cell lines (Park, Y. et al., *J Nat. Prod.* 2003, 66, 1495-1498). Other studies suggest that the cytotoxicity of psammaplin A might be related to the inhibitory effect it has on the fundamental cellular process-DNA replication, and one of the main target molecules of psammaplin A could be pol α-primase (Jiang, Y. et al., *BMC Cancer* 2004, 4:70). Recently, 1 has been found as a potent inhibitor of APN, a metalloproteinase required for tumor invasion and angiogenesis (Shima, J. S. et al., J. *Cancer Letters* 2004, 203, 163-169).

Among the reported bioactivities attributed to psammaplin A (1), the most important is perhaps its ability to inhibit the enzymes that deacetylate histones, known as histone deacetylases (HDAC) (IC50 4.2 nM, in vitro cell-free enzyme assay) (Piña, I. C. et al., *J. Org. Chem.* 2003, 68, 3866-3873). Several HDAC inhibitors are currently undergoing clinical trials as potential molecular-targeted chemotherapeutical agents for cancer (Remiszewski, S. W. *Curr. Med. Chem.* 2003, 10, 2393-2402). Although 1 inhibited tumour growth both in vitro and in vivo, its poor physiological stability prevented its development as a drug. The instability of 1 under physiological conditions (or poor cell membrane penetration) may explain why inhibition of HDAC in a cell-based assay requires a concentration of 1 that is 1800 times greater than the concentration required to inhibit HDAC in an enzyme-based assay.

During the course of developing potent and selective HDAC inhibitors, it was demonstrated that amide moieties derived from hetero aromatic acids might serve as useful terminal residues of HDAC inhibitors. The synthesis of a series of heterocyclic-amide hydroxamic acids demonstrated the high potency of indole-amides, in particular 2-substituted indole-carboxamides, as HDACis (Dai, Y. et al.; *Bioorg. Med. Chem. Lett.* 2003, 13, 1897-1901).

An aim of the invention was to obtain new molecules with a structure analogous to that of psammaplin A and a significant biological activity on cancerous cell lines.

An object of the invention is a molecule responding to formula (I) here-under:

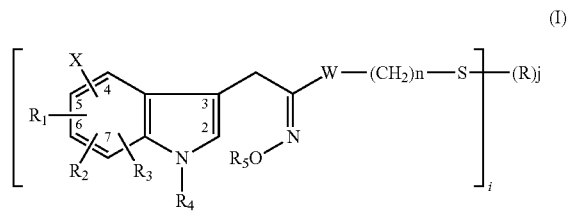

Wherein:

n is an integer selected from 1, 2, 3, 4, 5, 6, 7, 8;
i is an integer selected from 1, 2;
j is an integer selected from 0, 1;
when i=2, then j=0 and when i=1, then j=1;
X is a halogen atom;
W is a linker selected from: —CO—NH—, —NH—CO—, —CO—O—, —O—CO—, —CO—S—, —S—CO—, —CH=CH—, a covalent link;
R is a group selected from: a hydrogen atom, a $C_1$-$C_6$ alkyl group, a $C_1$-$C_6$ carboxyalkyl group;
$R_1$, $R_2$, $R_3$, identical or different are selected from: a hydrogen atom, a $C_1$-$C_6$ alkyl group, a $C_1$-$C_6$ halogenoalkyl group, a halogen atom, a hydroxyl group, a $C_1$-$C_6$ alcoxy group, a $C_1$-$C_6$ aminoalkyl group, a $C_1$-$C_6$ saturated heterocycloalkyl group, a $C_6$-$C_{12}$ aryl group, a $C_6$-$C_{20}$ aralkyl group, a $C_4$-$C_{12}$ heteroaryl group;

$R_4$ is selected from: a hydrogen atom, a $C_1$-$C_6$ alkyl group, a $C_2$-$C_6$ acyl group, a $C_6$-$C_{12}$ aryl group, a $C_6$-$C_{20}$ aralkyl group, a $C_4$-$C_{12}$ heteroaryl group;

$R_5$ is selected from: a hydrogen atom, a $C_1$-$C_6$ alkyl group, a $C_6$-$C_{20}$ aralkyl group;

and its pharmaceutically acceptable salts.

A halogen atom is an atom selected from: Cl, F, Br, I.

A $C_1$-$C_6$ alkyl group means an alkyl chain, linear, branched or cyclic, comprising 1, 2, 3, 4, 5 or 6 atoms of carbon.

A $C_1$-$C_6$ halogenoalkyl group means an alkyl chain, linear, branched or cyclic, comprising 1, 2, 3, 4, 5 or 6 atoms of carbon and at least one halogen atom.

A $C_1$-$C_6$ alcoxy group means an —O-alkyl group, wherein the alkyl chain, linear, branched or cyclic, comprises 1, 2, 3, 4, 5 or 6 atoms of carbon.

A $C_1$-$C_6$ aminoalkyl group means an —NH-alkyl group, or an —N-di-alkyl group, wherein the alkyl chain, linear, branched or cyclic, comprise(s) 1, 2, 3, 4, 5 or 6 atoms of carbon.

A $C_1$-$C_6$ saturated heterocycloalkyl group is a saturated cyclic chain comprising from 1, 2, 3, 4, 5 or 6 carbon atoms and one or two heteroatoms, like N, O, S, like for example a pyrrolidine, a piperidine, a tetrahydrofurane.

A $C_6$-$C_{12}$ aryl group is an aromatic group comprising 6, 7, 8, 9, 10, 11 or 12 carbon atoms, like a phenyl or a naphtyl group.

A $C_6$-$C_{20}$ aralkyl group comprises an alkyl chain and at least one aromatic group and from 6 to 20 carbon atoms, like a benzyl group or a trityl group.

A $C_4$-$C_{12}$ heteroaryl group is an aromatic group comprising 4, 5, 6, 7, 8, 9, 10, 11 or 12 carbon atoms and one or two heteroatoms like N, O, S, like for example a pyridin, a furan, a pyrimidin.

A $C_2$-$C_6$ acyl group is a —CO-alkyl group wherein the alkyl chain comprises 1, 2, 3, 4 or 5 carbon atoms.

Preferably, one or several of the following conditions are met:

n is an integer selected from 2, 3, 4, 5, 6;

i is 2;

j is 0;

X is Br;

W is —CO—NH—;

$R_1$, $R_2$, $R_3$ are hydrogen atoms;

$R_4$ is H, $R_5$ is H.

Favorite molecules are those included in the list here-under:

UVI 5008

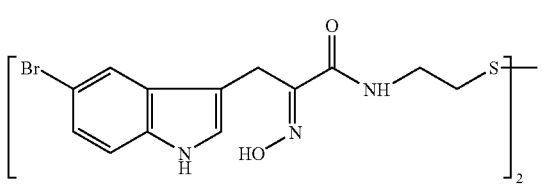

-continued

UVI 5009

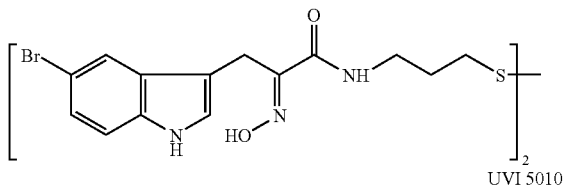

UVI 5010

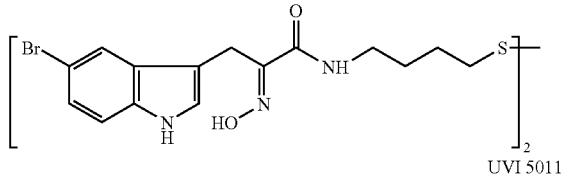

UVI 5011

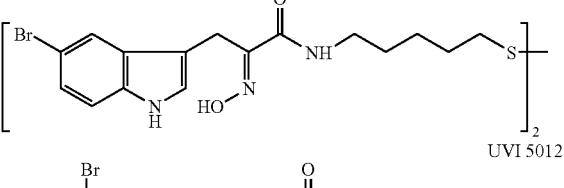

UVI 5012

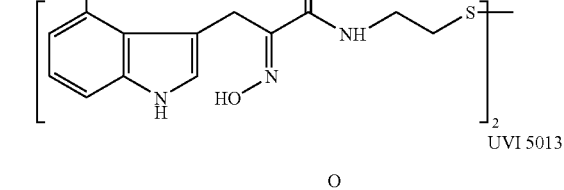

UVI 5013

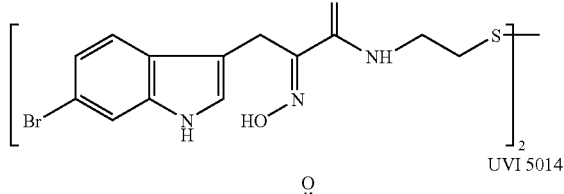

UVI 5014

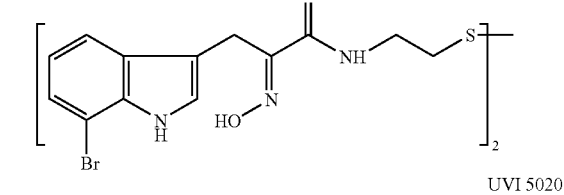

UVI 5020

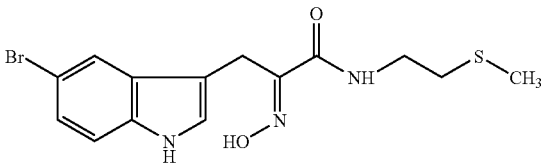

Surprisingly, the inventors have discovered that the molecules responding to formula (I) have the property of inhibiting at least one, better two, and even preferably three steps of the cell cycle of cancer cells. Especially, the molecules of formula (I) have one or more of the following properties when in contact with cancer cells:

they induce cell cycle arrest, they induce apoptosis, they act as inhibitors of histone deacetylases (HDACs), they act as inhibitors of DNA methyltransferases (DN-MTs)

they induce expression of the TNF-related apoptosis inducing ligand TRAIL, they act as inhibitors of human SIRT1 and SIRT2.

Some molecules of formula (I) are also useful as intermediates for the synthesis of the biologically more active molecules.

Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiologically acceptable anion, for example, tosylate, methanesulfonate, acetate, citrate, malonate, tartrate, succinate, benzoate, ascorbate, alpha-ketoglutarate, and alpha-glycerophosphate. Suitable inorganic salts may also be formed, including sulfate, nitrate, bicarbonate, and carbonate salts. Pharmaceutically acceptable salts may be obtained using standard procedures well known in the art.

An object of the invention is a medicament or a pharmaceutical composition comprising an effective amount of a molecule of formula (I) or a salt thereof in a pharmaceutically acceptable support.

According to the invention, the composition includes the appropriate carriers, such as water, and is formulated for the desired route of administration to an individual in need thereof. Optionally the compound is administered in combination or alternation with at least one additional therapeutic agent for the treatment of tumors or cancer.

Another object of the invention is the use of a molecule of formula (I) for the preparation of a medicament for preventing and/or treating a tumour or a cancer in an individual in need thereof. This use is especially concerned with the prevention and/or treatment of a cancer selected from: lung, ovarian, central nervous system (CNS), skin, and colon cancer or leukemia.

As used herein, the terms cancer and cancerous refer to or describe the physiological condition in mammals that is typically characterized by unregulated cell growth, and especially proliferative disorders. Examples of such proliferative disorders include, among others, cancers such as carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer (hepatic carcinoma), bladder cancer, colorectal cancer, endometrial carcinoma, kidney cancer, and thyroid cancer.

As used herein, the term tumour refers to a neoplastic cell growth and proliferation, whether malignant or benign, and all pre-cancerous and cancerous cells and tissues. Notably, a cancer may be characterized by a solid tumour mass. The solid tumour mass, if present, may be a primary tumour mass. A primary tumour mass refers to a growth of cancer cells in a tissue resulting from the transformation of a normal cell of that tissue.

The dosage and rhythm of administration of the medicament of the invention is adapted in view of the biological activity of the selected molecule of formula (I), of the age and weight of the patient, of the type and importance of the cancer and/or tumour, and of the route of administration chosen.

Another object of the invention is a method for the synthesis of the molecules of formula (I).

Hoshino et al. (*Bioorg. Med. Chem. Lett.* 1992, 2, 1561-1562) have reported the synthesis of 1 from 3-bromotyrosine in 4 steps (Scheme 1). Psammaplin A (1) was obtained in 23% yield over the 4 steps.

Scheme 1.

Scheme 1

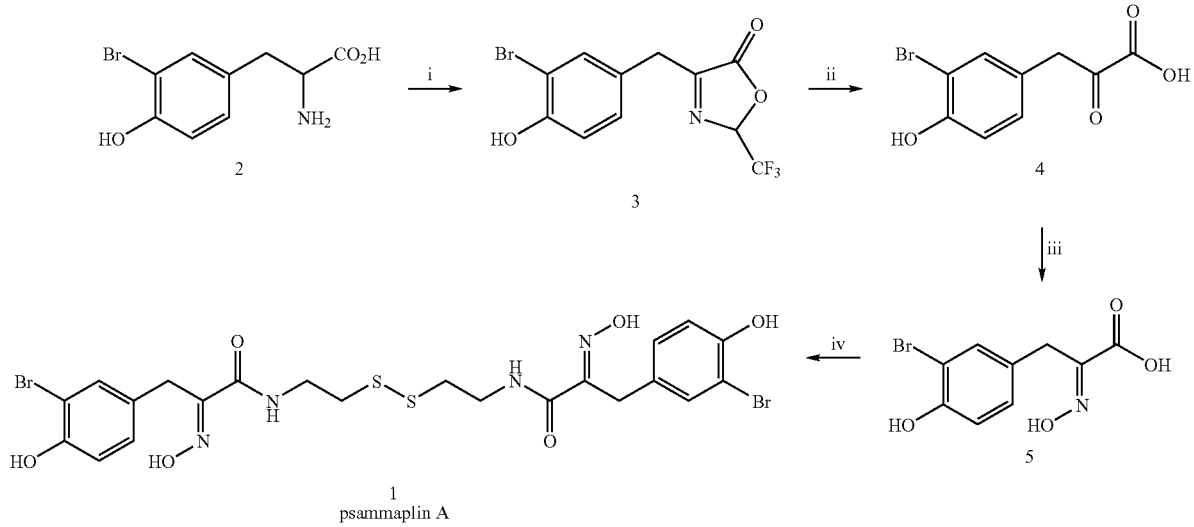

1
psammaplin A

Reagents and conditions: (i) (CF$_3$CO)$_2$O, 80-120° C., 1 h (61%); (ii) 70% aq TFA, 25° C., 12 h (97%); (iii) HONH$_2$•HCl, AcONa, EtOH, 25° C. (57%); (iv) DDC, N-hydroxyphthalimide, Et$_3$N, cystamine, 1,4-dioxane-MeOH, 25° C., 12 h (67%).

The essential features of Hoshino's approach were subsequently incorporated into a general approach to psammaplin A-type derivatives reported by Nicolaou, (Nicolaou, K. et al., J. Chem.-Eur. J. 2001, 7, 4280-4295) shown in Scheme 2. Psammaplin 1 analogues were obtained in 36% yield over the 4 steps from 4 (Nicholaou, G. M. et al., A. Bioorg. Med. Chem. Lett. 2002, 12, 2487-2490). Nicolaou's approach was exploited in the preparation, via catalytically-induced disulfide exchange, of a 3828-membered library of psammaplin A analogues which were screened for their antibacterial properties (Nicolaou, G. M. et al., Bioorg. Med. Chem. Lett. 2002, 12, 2487-2490).

These total syntheses gave psammaplin A with a poor global yield. A recent synthesis of psammaplin A should be mentioned which avoids the protection-deprotection steps of the oxime group and proceeds in higher yield (Godert, A. M. et al., Bioorg. Med. Chem. Lett. 2006, 16, 3330-3333). Another aim of the invention was to find a method for the synthesis of psammaplin A derivatives which would be simple, give high yields and which could be easily industrialized.

Now the inventors have found a novel method for the synthesis of psammaplin A derivatives of the 2-substituted indole-carboxamide type, which method is fast, simple and gives high yields.

In the case when W=—CO—NH—, the method of the invention is characterized in that it comprises at least one step as depicted in scheme 3, wherein:

Scheme 2

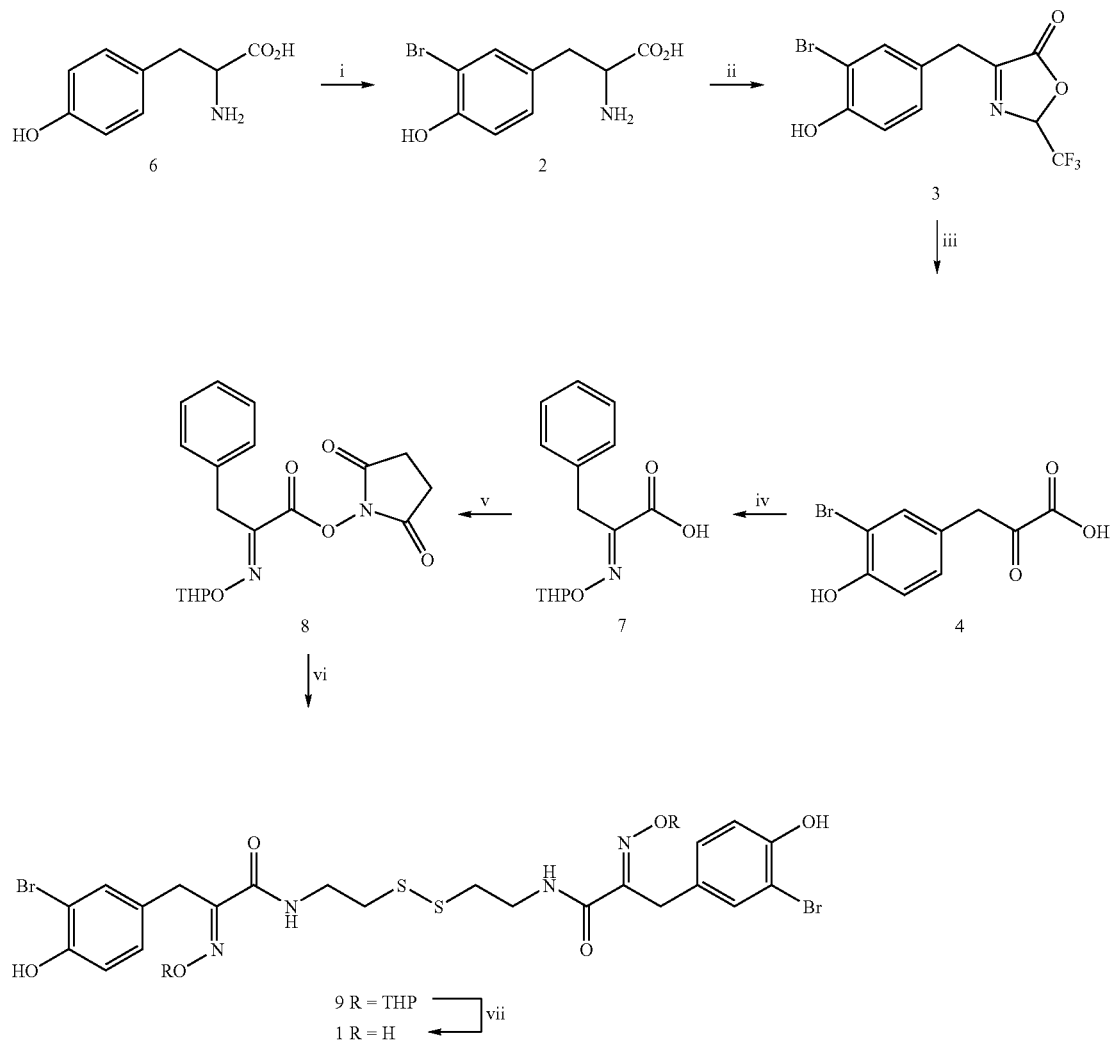

Reagents and conditions: (i) KBr—KBrO$_3$, H$_2$O, 23° C., 12 h (81%); (ii) TFAA, 80° C., 12 h; (iii) 70% aq. TFA, 23° C., 12 h (60%, 2 steps); (iv) THP-ONH$_2$, EtOH, 23° C., 12 h; (v) EDC, NHS, 1,4-dioxane, 23° C., 2 h; (vi) Et$_3$N, cystamine•HCl, 1,4-dioxane-MeOH, 23° C., 2 h; (vii) HCl, CH$_2$Cl$_2$-MeOH, 60° C., 2 h (36% from 7).

Scheme 3

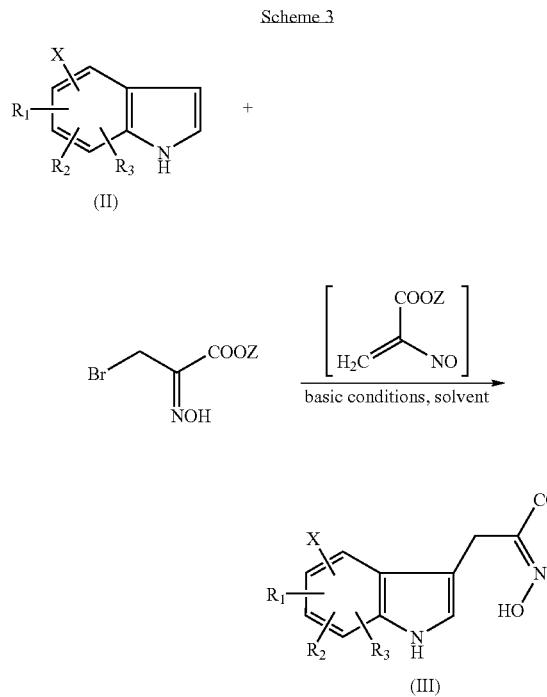

The synthesis depicted in Scheme 3 started with alkylation of the indol (II) with approximately one equivalent of nitrosoacrylate $CH_2=C(NO)-COOZ$, in which Z represents a group selected from: $C_1$-$C_6$ alkyl, phenyl, aryl group, like for example a benzyl group (Gilchrist, T. L.; Roberts T. G. *J. Chem. Soc. Perkin Trans I* 1983, 1283-1292), generated in situ from the corresponding bromo-oxime. Said bromo-oxime is prepared in a known manner by the reaction of ethyl bromopyruvate with hydroxylamine hydrochloride. Preferably, the reaction is conducted in a basic medium, in a solvent, at ambient temperature. The solvent can be a chlorinated solvent like $CH_2Cl_2$, $CHCl_3$, or $ClCH_2$—$CH_2Cl$, or the solvent can be nitroethane, or dioxane. The base used can be a metal carbonate, a metal bicarbonate or sodium hydride. Preferably, we used a carbonate salt, like $K_2CO_3$ or $Na_2CO_3$. The advance of the reaction is followed by TLC or HPLC and can last one to several hours, depending on the substituents, the solvent and the temperature. Advantageously Z is selected from alkyl groups (primary, tertiary) or can be a benzyl group. Preferably Z is ethyl.

When W is different from —CO—NH—, the skilled professional will easily adapt this method by using his general knowledge. For example, after protection of the oxime and saponification, borane reduction of the acid to the alcohol would allow to prepare the aldehydes and from them, by Horner Wadsworth Emmons reaction, the unsaturated analogue (W: CH=CH).

Advantageously, this first step is followed by the process depicted on Scheme 4:

Scheme 4

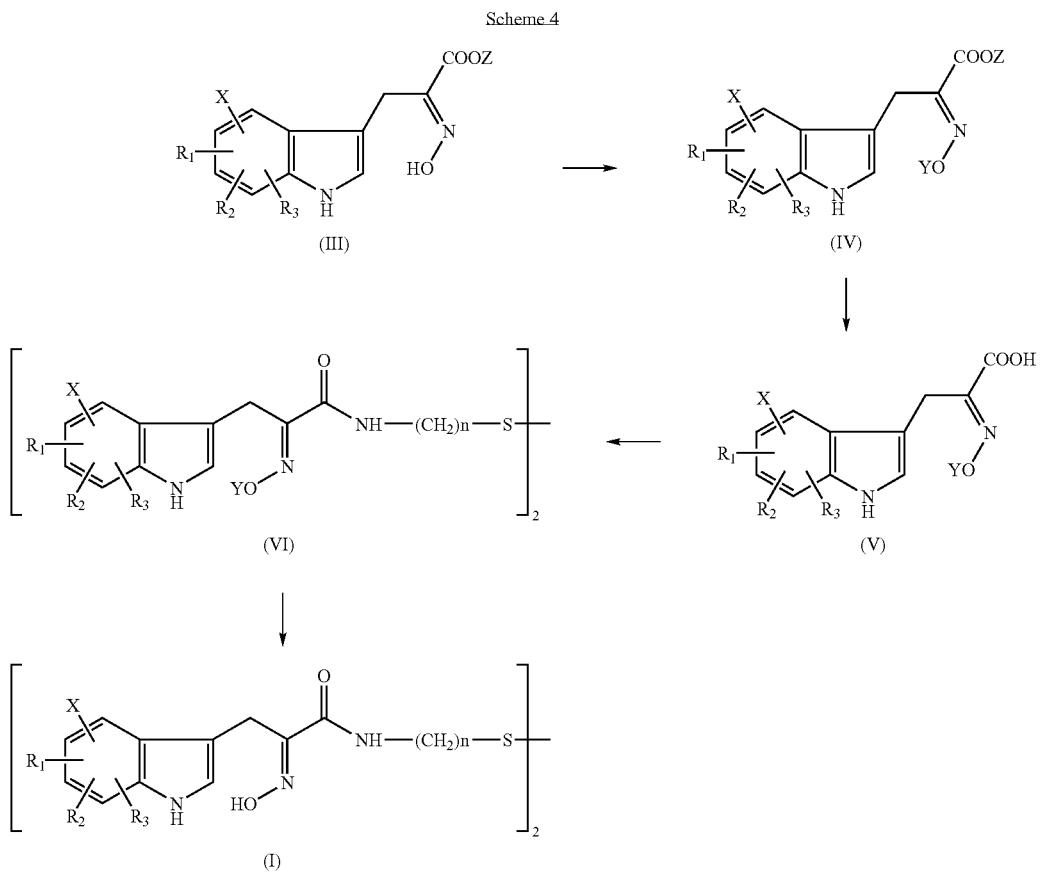

The oxime (III) is converted to compound (IV) by protection of the oxime function with an appropriate protective group Y, which can be selected from trityl, benzyl, methoxy methyl, methoxy ethoxy methyl, 2-tetrahydropyranyl. Preferably Y is a trityl group. Then the ester function —COOZ is deprotected to —COOH by an appropriate treatment to give the molecule (V). This molecule is then reacted with the appropriate di-amine $H_2N-(CH_2)n-S-S-(CH_2)n-NH_2$ to give (VI), and the oxime function is then liberated to produce the molecule of formula (I).

When i=j=1 this method is adapted to produce the corresponding molecules of formula (I) according to scheme 5:

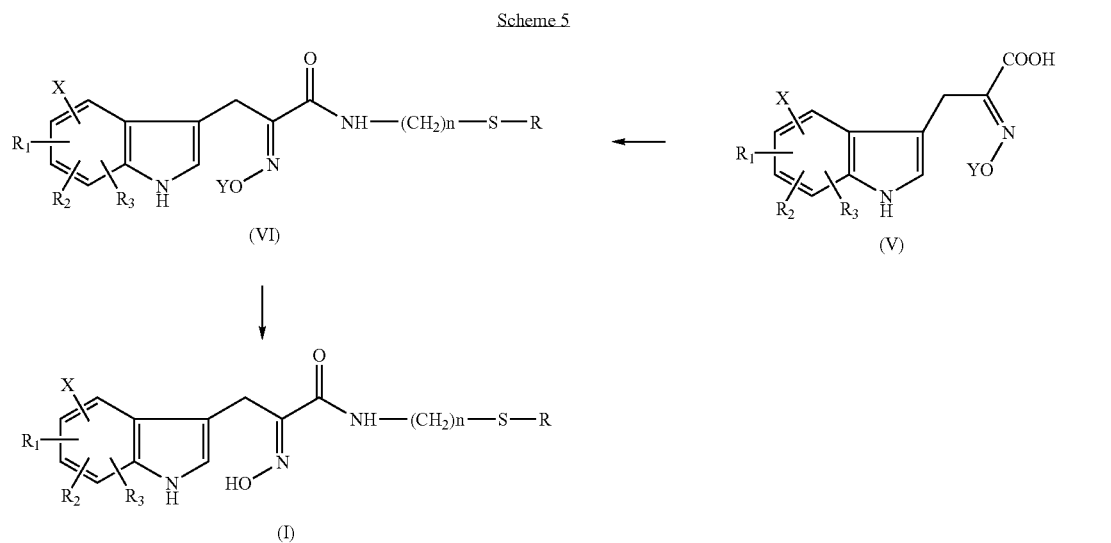

Scheme 5

Compound (VI) is reacted with the amine $H_2N-(CH_2)n-S-R$ and the oxime function is deprotected to give (I).

The biological effects of psammaplin A derivatives in cellular cancer models were investigated:

Induction of Cell Cycle Arrest and Apoptosis:

The molecules of the invention induced inhibition of proliferation (FIG. 1a) and/or apoptosis (FIG. 1b) in U937 acute myeloid leukemia cell line (FIG. 1). They also increase the expression of the cell cycle inhibitors $p21^{WAF1/CIP1}$, known to be required for G1 and sustained G2 arrests (Bunz, F. et al., Science 282, 1497-501 (1998)) (FIG. 1c).

Figure 6:
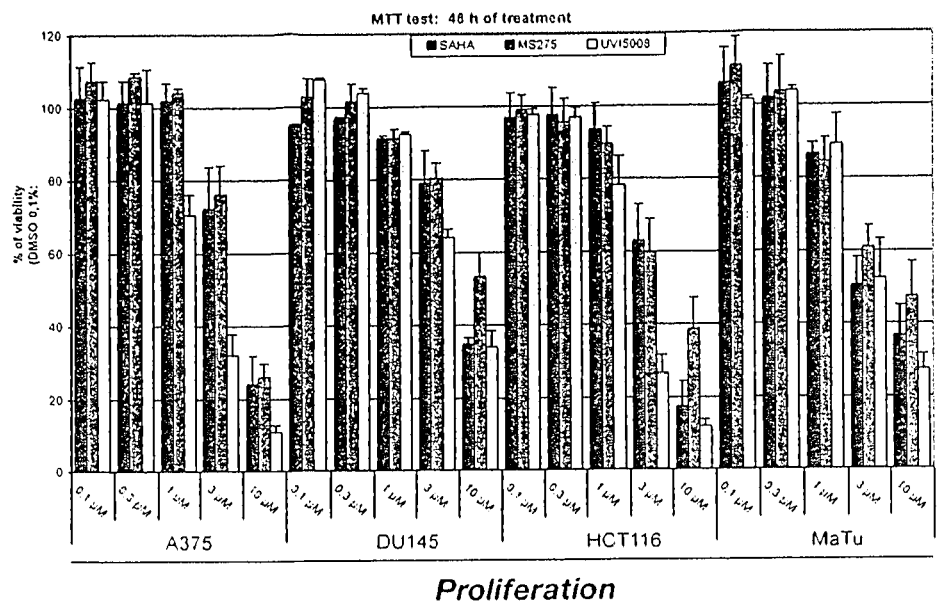
Figure 6:
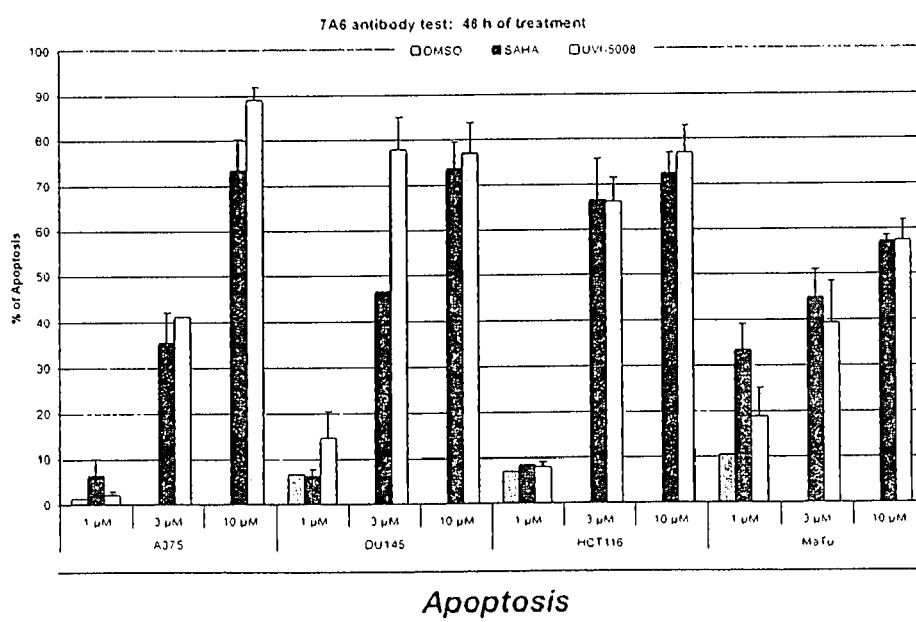

The anti-proliferative and apoptogenic action of psammaplin A and its two derivatives 5008 and 5010 was confirmed also in solid cancer cell line such as breast cancer cells (ZR75.1) and prostate cancer cells (LnCap; data not shown; see also FIG. 6).

UVI5008 is a Powerful HDAC Inhibitor:

Histone histone H3 acetylation (FIG. 1d) and HDAC inhibition (FIG. 1e, lanes 6, 7) were observed.

UVI5008 Inhibits DNA Methylation in the Promoter Region of the Tumour Suppressor Genes $p16^{INK4a}$ and RARβ2:

To study if UVI5008 would have additional activities the possible inhibition of the DNA methylation of the promoters of tumor suppressor genes was studied. Using methylation-specific PCR (MSP) a significant increase of unmethylated RARβ2 was observed (FIG. 2a). Concomitantly, the amount of unmethylated $p16^{INK4a}$ promoter DNA increased (FIG. 2b). In keeping with the demethylation of the $p16^{INK4a}$ promoter the $p16^{INK4a}$ gene expression was de-silenced by exposure to molecules of the invention, and this expression was comparable to that seen with the combination of 5-deazacytidine with SAHA (FIG. 2c).

Finally, using in vitro DNA methyltransferase (DNMT) assays it was confirmed that molecules of formula (I) are DNMT inhibitors (FIG. 2d).

UVI5008 Alters the Acetylation Status of Chromatin at the TRAIL Locus which Encodes a Tumor-Selective Apoptosis Inducing Death Ligand:

Notably, exposure of U937 myeloid cells to molecules of formula (I) leads to a rapid dramatic H3K9 acetylation of the chromatin at the TRAIL promoter and with a delayed kinetics also at the first intron (FIG. 5a). This "activating" chromatin mark correlates with increased expression both at the mRNA (FIG. 5b) and protein (FIG. 5b) levels, as shown by RT-PCR and ELISA assays, respectively.

Figure 7:
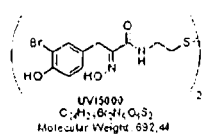
Figure 7:
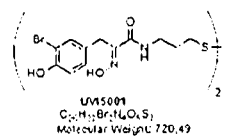
Figure 7:
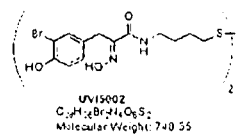
Figure 7:
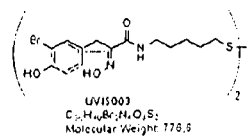
Figure 7:
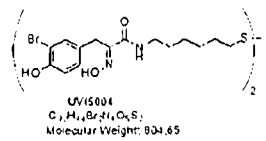
Figure 7:
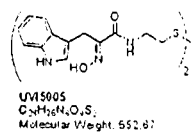
Figure 7:
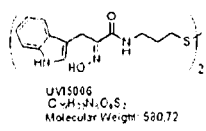
Figure 7:
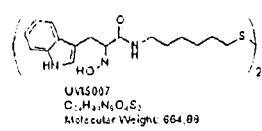
Figure 7:
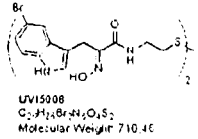
Figure 7:
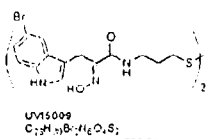
Figure 7:
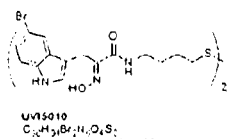
Figure 7:
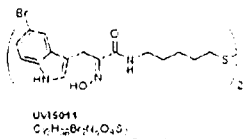
Figure 7:
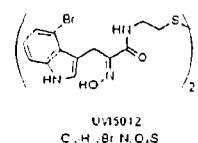
Figure 7:
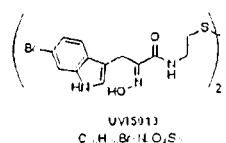
Figure 7:
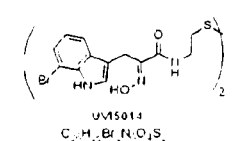
Figure 7:
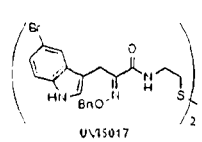
Figure 7:
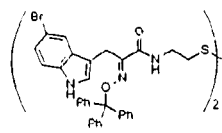
Figure 7:
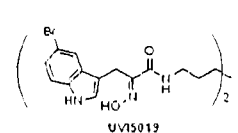
Figure 7:
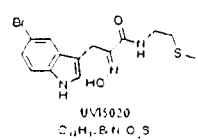
Figure 7:
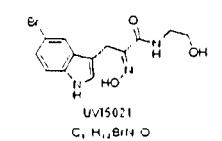
Figure 7:
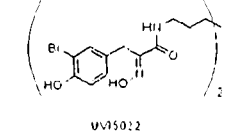
Figure 7:
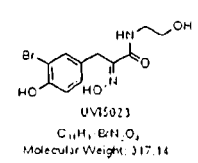

Structure-Activity-Relationship (SAR) Studies of HDAC Activity:

To initiate a SAR study of the above described HDAC inhibitor activities of UVI5008 a series of derivatives was synthesized (FIG. 7). The activity readouts that were systematically investigated were cell cycle arrest and $p21^{WAF1/CIP1}$ induction, induction of differentiation and acetylation of targets (in this case a-tubulin).

Figure 4:
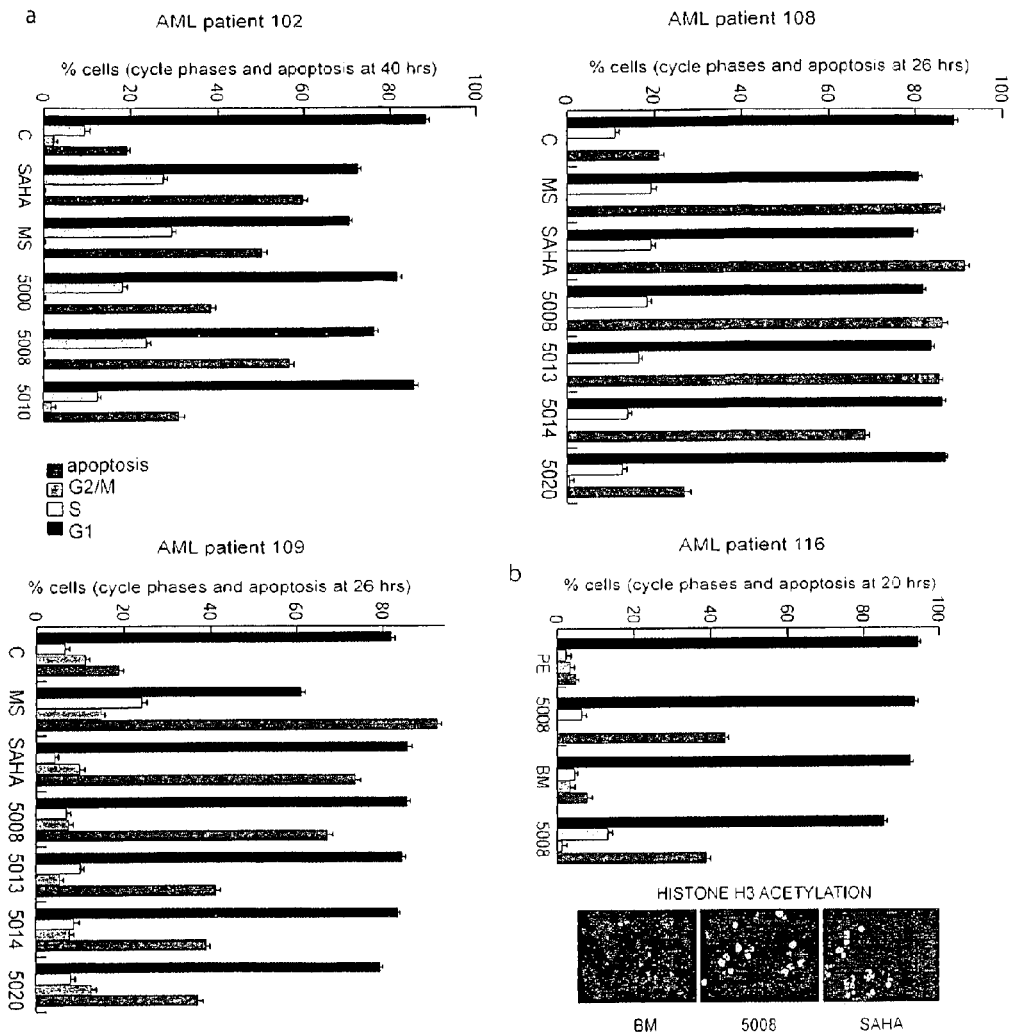

Psammaplin A Derivatives Induce Apoptosis in AML Patient Blasts:

The intriguing anticancer potential of some psammaplin A derivatives prompted us to test their activity in ex vivo AML patient blasts. As shown in FIG. 4, the molecules of formula (I) induced cell cycle arrest and apoptosis in the blasts, as measured by caspase 3 activation assays in 4 independent ex vivo cultures of different patients (AML patients #102, #108, #109, #116). All tested derivatives showed an apoptotic activity in two different samples of patient blasts.

EXPERIMENTAL PART

I—Figures

FIG. 1: a) Cell cycle analysis of U937 cells treated for 30 hrs with the indicated compounds used at 1 and 5 μM; b) Caspase 3 apoptotic assay of the indicated compounds after 24 hrs of treatment in the U937 cells; c) Tubulin acetylation and p21 expression levels at 6 and 16 hrs after treatment with the indicated compounds; total tubulin expression levels are used for equal loading; d) Histone H3 acetylation and K9 H3 methylation expression levels at 6 and 16 hrs after treatment with the indicated compounds; total tubulin expression levels are used for equal loading; e) K9, K14, K18 histone H3 acetylation expression levels at 6 and 16 hrs after treatment with the indicated compounds; total ERKs expression levels are used for equal loading; f) HDAC1 enzymatic assay: IP-HDAC1 is incubated with the indicated inhibitors for 24 Hrs; activity is measured as $^3$H-acetyl release; g) HDAC4 enzymatic assay: IP-HDAC4 is incubated with the indicated inhibitors for 24 hrs; activity is measured as $^3$H-acetyl release.

Figure 2:
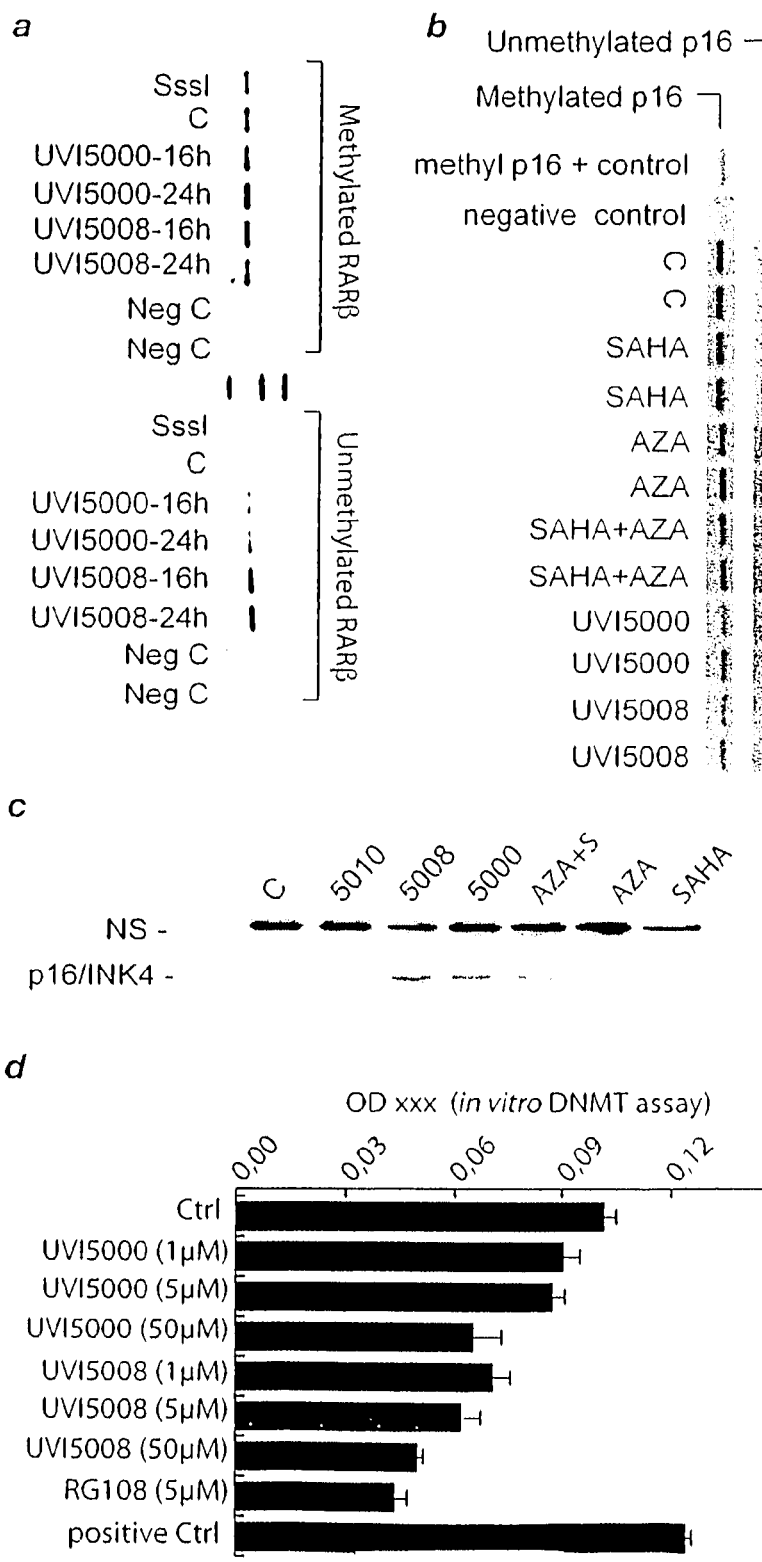
Figure 3:
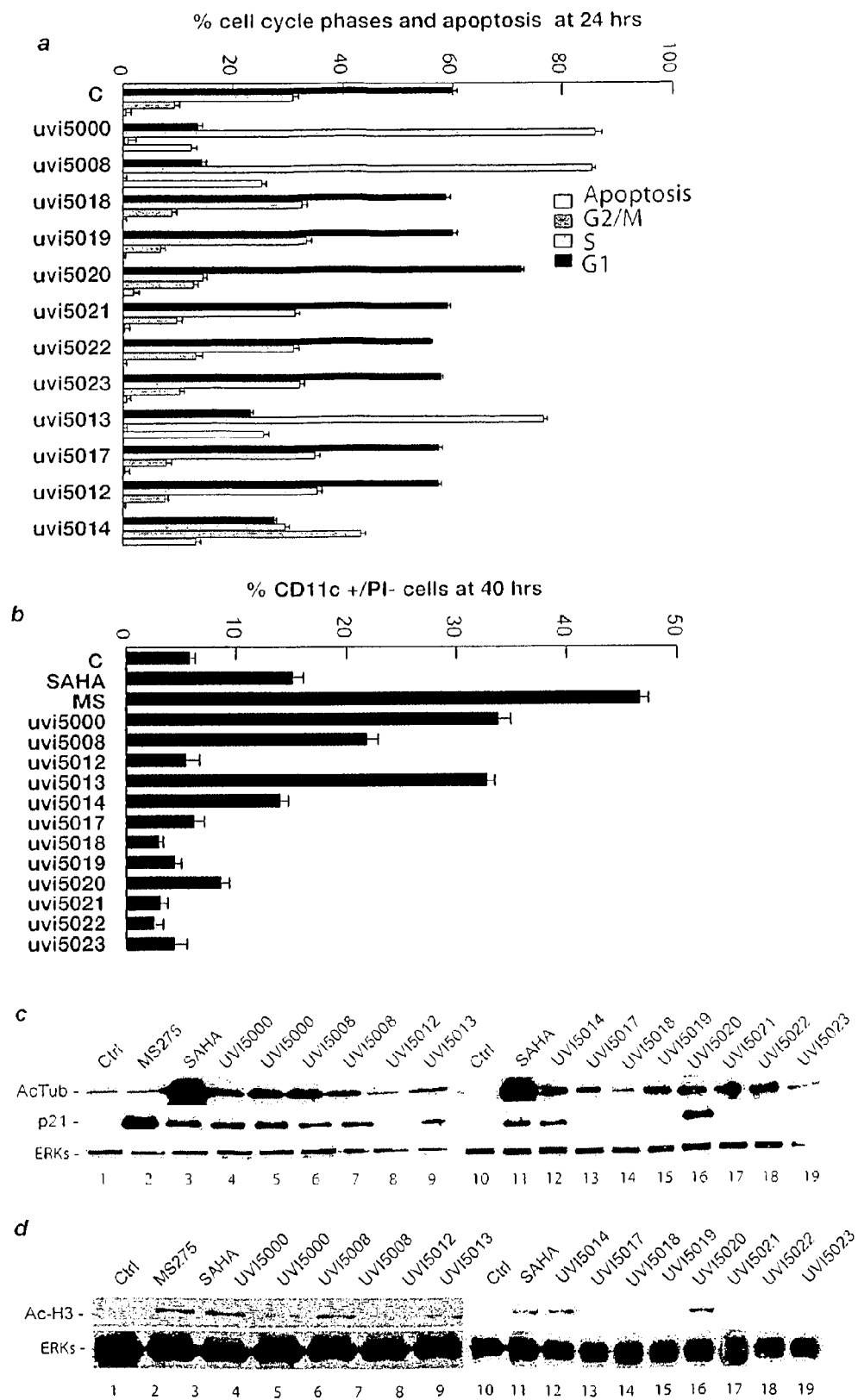

FIG. 2: a) Methylation specific PCR for the RARβ gene after 16 and 24 hrs of treatment with the indicated compounds; b) Methylation specific PCR for the p16 gene after 24 hrs of the indicated treatments. Samples are representative of real duplicates; c) p16 expression levels in U937 cells after 24 hrs with the indicated treatments; d) DNMT enzymatic in vitro assay carried out with 1.5 and 50 µM of the indicated compounds;

FIG. 3: a) Cell cycle and apoptosis analysis carried out in U937 cells after 24 hrs with the indicated compounds; values are media of independent triplicates; b) CD11c expression analysis carried out in U937 cells with the indicated compounds; values are media of independent duplicates; c) Tubuline acetylation and p21 expression levels in U937 cells after 24 hrs with the indicated treatments; total ERKs expression levels are used for equal loading; d) acetylation of histone H3 under the conditions indicated in (c).

FIG. 4: a) Cell cycle analyses and apoptosis carried out in ex vivo samples from AML patients identified with numbers; b) Cell cycle analysis, apoptosis and histone H3 acetylation levels of #116 AML cells after 20 hrs is of the indicated treatments.

Figure 5:
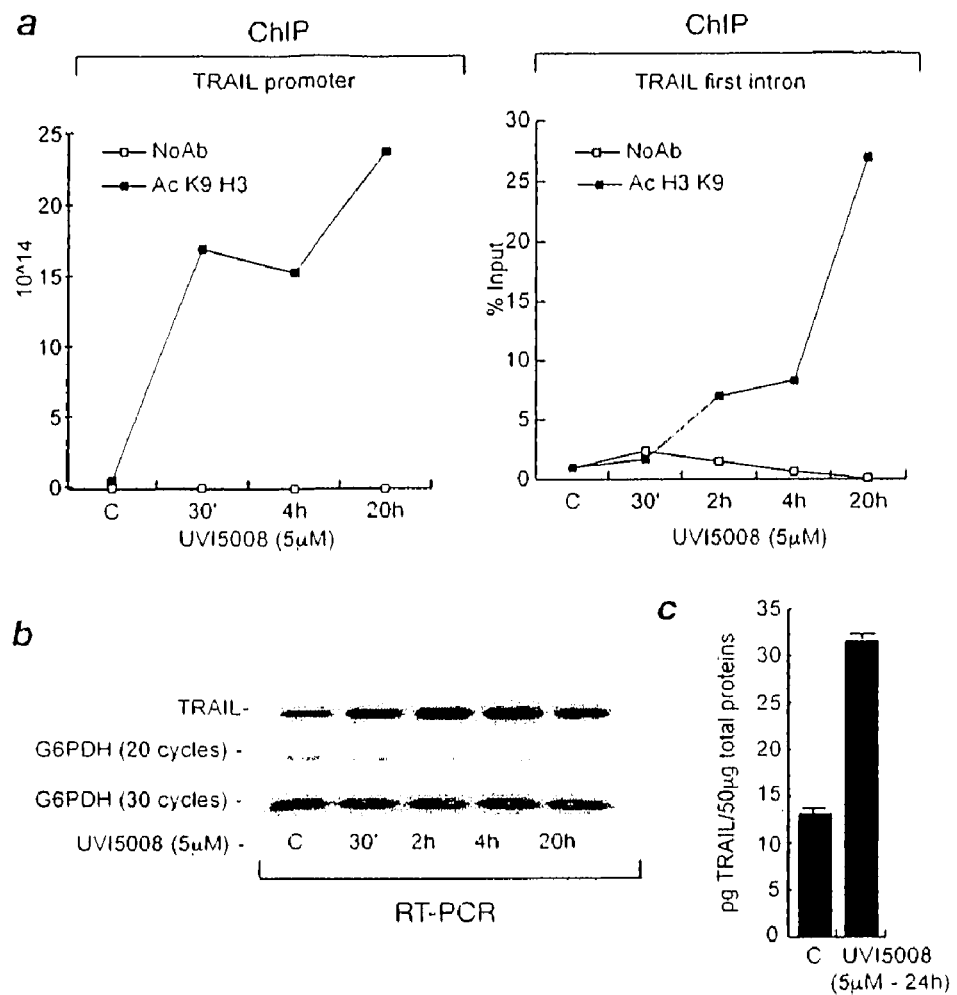

FIG. 5: a) Analysis of the histone H3 acetylation levels on the TRAIL promoter regulatory region and on the TRAIL gene first intron carried out Chip and qPCR in U937 cells after the indicated time course with UVI5008; the 'NoAb' represents the negative control; b) TRAIL mRNA expression after the indicated times of incubation with UVI5008; G6PDH levels have been used for equal loading; c) TRAIL protein expression levels measured by ELISA assay in U937 cells after 24 hrs treatment with UVI5008.

FIG. 6: Sensitivity of A375, DU145, HCT116 and MaTu cell lines to HDAC inhibitors. Cells were incubated in the presence of SAHA, MS275 or UVI5008 (0.1 µM, 0.3 µM, 1 µM, 3 µM, 10 µM). (a) Cell growth was determined after 48 hrs using the MTT test. Results are shown as percentage survival compared with the control and represent the mean±SD of triplicate measurements. (a) The percentage of apoptotic cells at 48 hrs culture was determined by APO2.7 staining. Results represent the mean±SD of triplicate measurements.

FIG. 7: List of tested molecules.

Figure 8A:
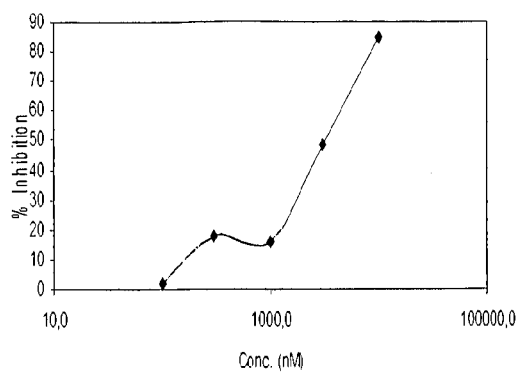
Figure 8A:
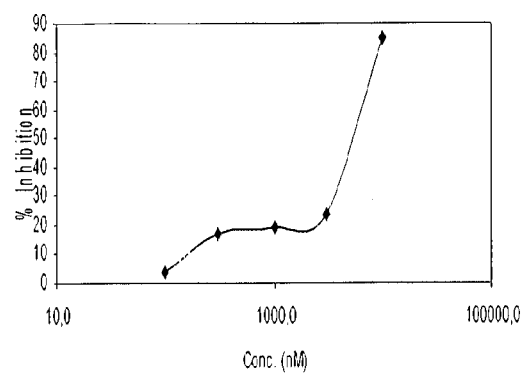
Figure 8A:
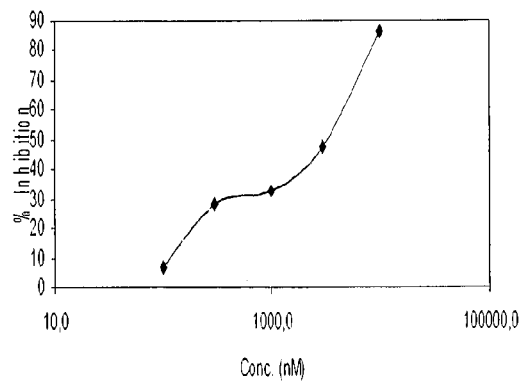

FIG. 8a: Dose response curves of A-375 cell lines with SAHA, MS-275 and UVI 5008, calculation of $IC_{50}$ values.

Figure 8B:
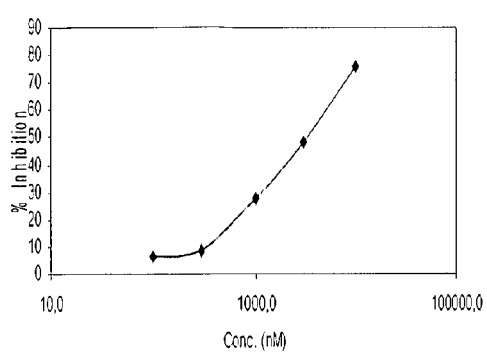
Figure 8B:
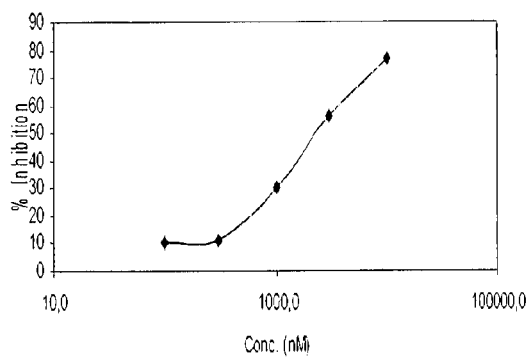
Figure 8B:
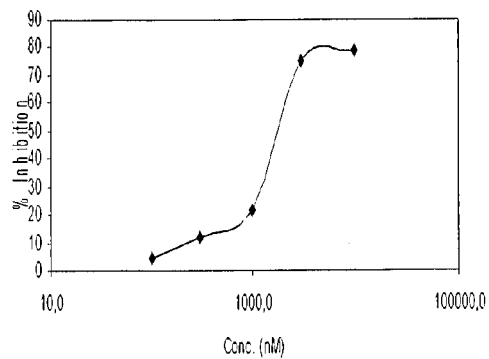

FIG. 8b: Dose response curves of HCT-116 cell lines with SAHA, MS-275 and UVI 5008, calculation of $IC_{50}$ values.

Figure 8C:
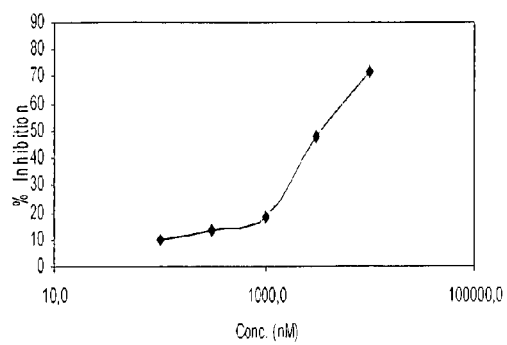
Figure 8C:
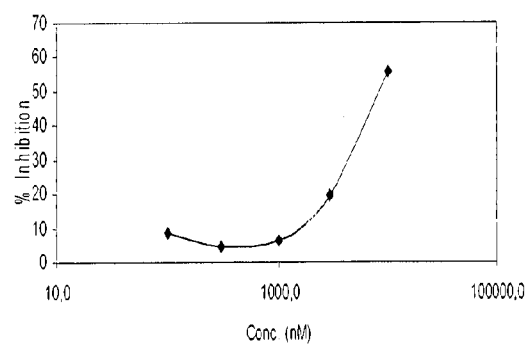
Figure 8C:
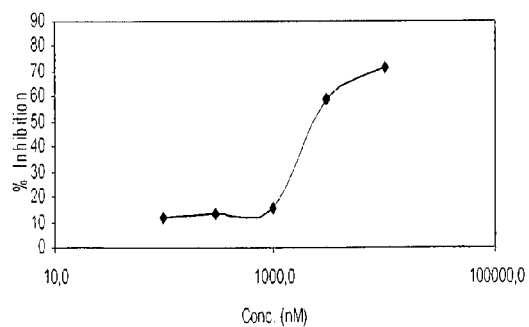

FIG. 8c: Dose response curves of DU-145 cell lines with SAHA, MS-275 and UVI 5008, calculation of $IC_{50}$ values.

Figure 9A:
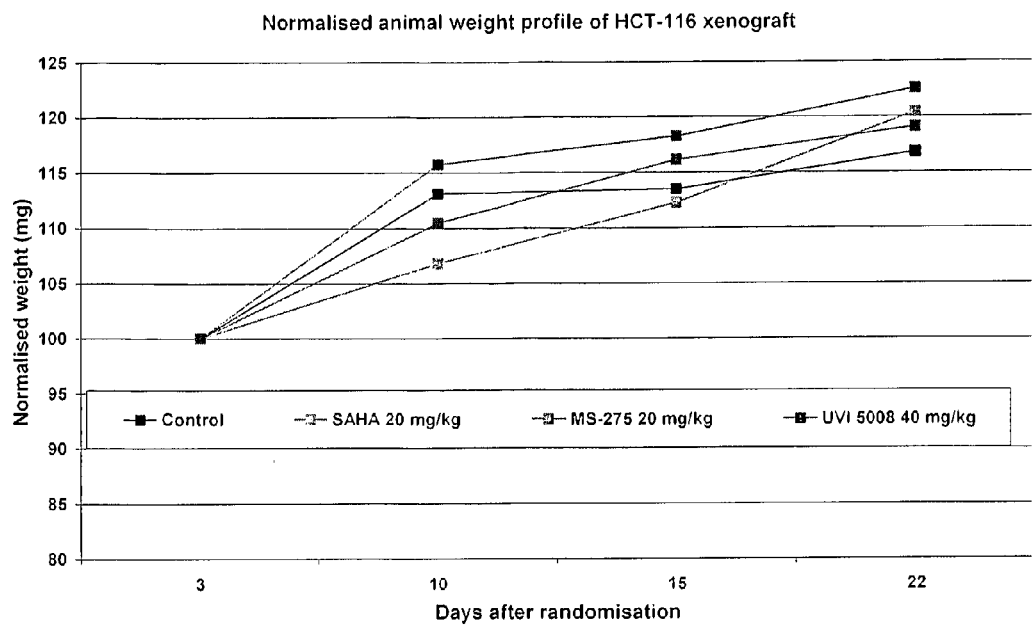

FIG. 9A: Normalized animal weight profile of HCT-116 xenograft.

Figure 9B:
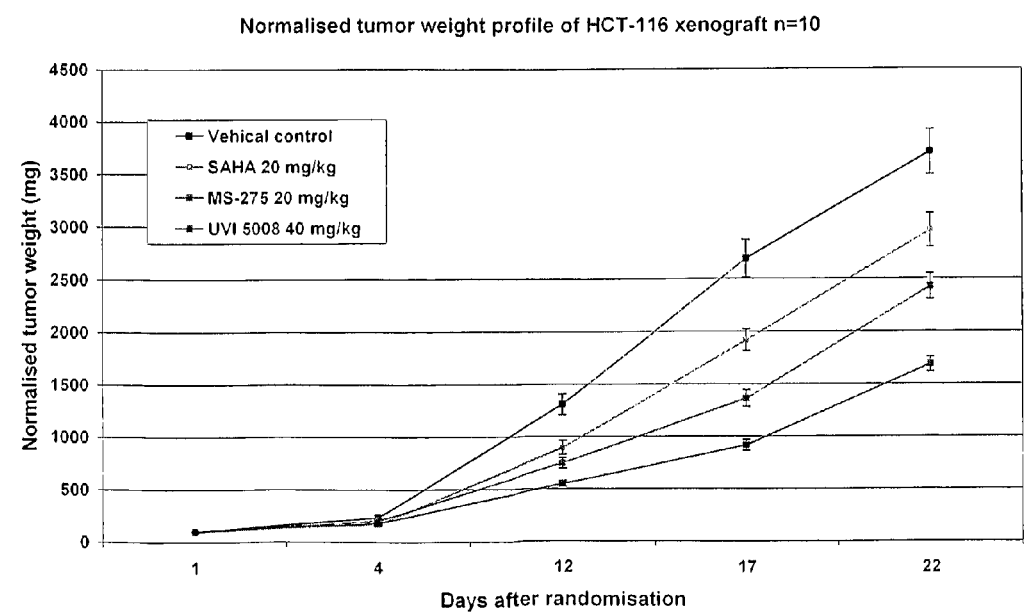

FIG. 9B: Normalized tumor weight profile of HCT-116 xenograft.

Figure 10A:
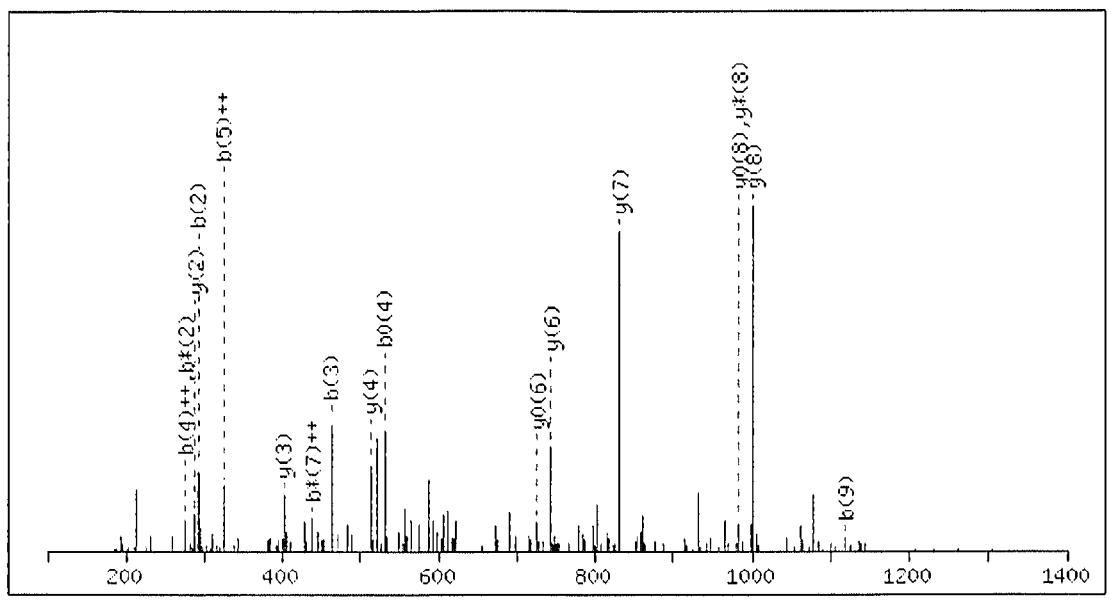

FIG. 10A: MS/MS fragmentation of YQKSTELLIR

FIG. 10B: MS identification of the H3K56ac

Figure 11:
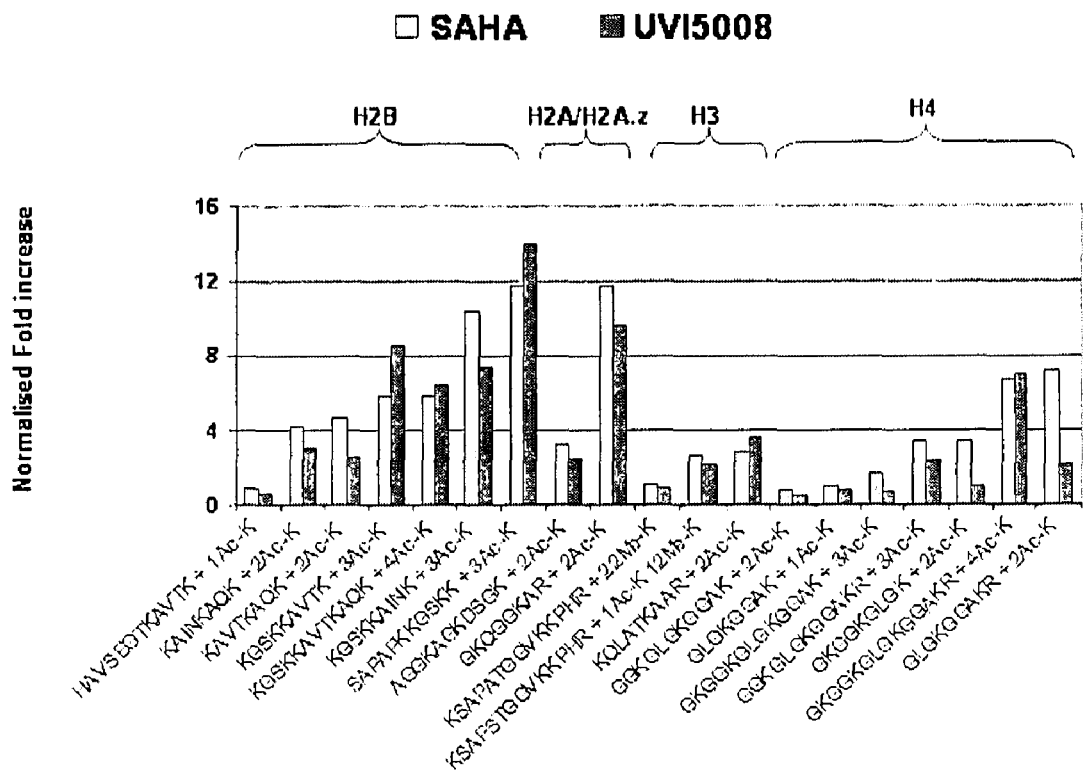

FIG. 11: SILAC proteomic analysis of a selected number of histone modifications.

Figure 12:
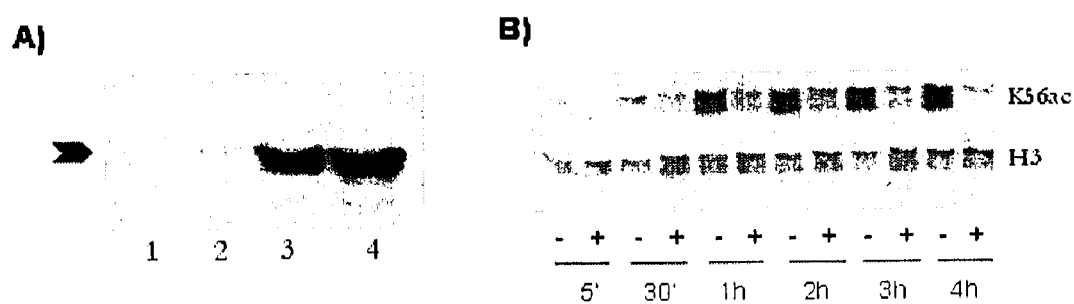

FIGS. 12: A and B Western blot analysis using an antibody that specifically recognizes acetylated K56 of H3.

Figure 13:
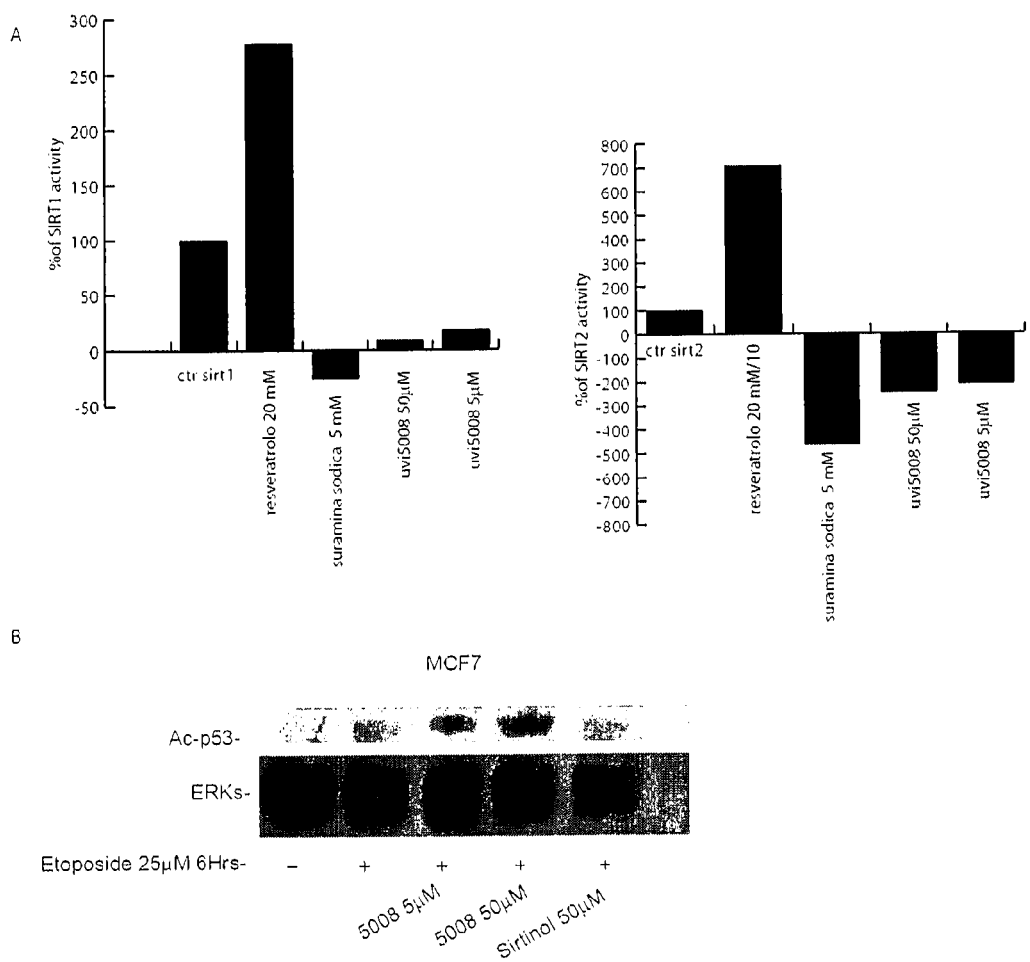

FIG. 13A: % of SIRT1 and SIRT2 activity with controls, sodium suramine, a sirtuin inhibitor, and resveratrol a SIRT1 activator, and with UVI5008 at concentrations of 50 µM and 5 µM.

FIG. 13B: western blot of MCF7 cells treated with etoposide alone or in presence of sirtinol (a known SIRT2 inhibitor) and with uvi5008 concentrations of 50 µM and 5 µM.

II—Synthesis

The synthesis (Scheme 6) started with alkylation of indole 21 with the nitrosoacrylate 22, (Gilchrist, T. L.; Roberts T. G. *J. Chem. Soc. Perkin Trans I* 1983, 1283-1292) generated in situ from bromo-oxime 23, prepared by the reaction of ethyl bromopyruvate 24 with hydroxylamine hydrochloride. The alkylation gave also cycloadducts 26 resulting from two consecutive attacks at the C3 position. They were separated by silica gel column chromatography (AcOEt/hexane 40:60). The reaction thus has potential as a method of alkylation of 3-substituted indoles. The yield of the reaction product 25 was increased to 67% after optimization (see Table).

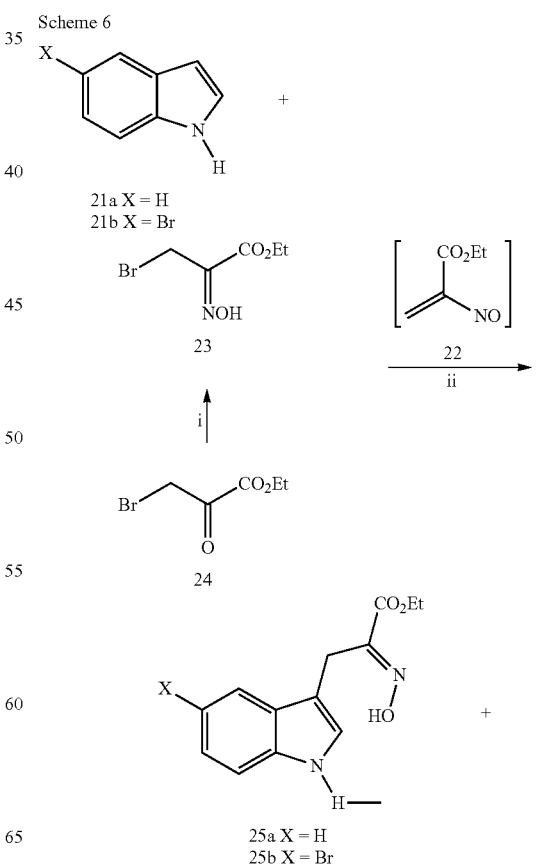

Scheme 6

-continued

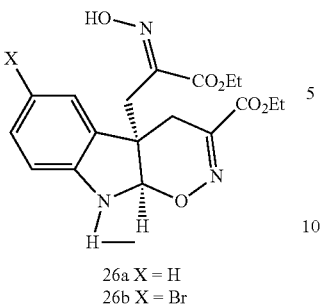

26a X = H
26b X = Br

Reagents and conditions: (i) 24, CHCl₃, NH₂OH•HCl, MeOH:H₂O (1:1), 22 h, 25° C. (86%). (ii) K₂CO₃, CH₂Cl₂, 25° C., 20 h (see Table 1).

TABLE 1

| Entry | 23 (equiv.) | Indol (equiv.) | Na₂CO₃ (equiv.) | Yield (%) 21:23:25:26 |
|---|---|---|---|---|
| 1 | 1 | 21a (1) | 0.4 | 17:11:40:4 |
| 2 | 1.75 | 21a (1) | 0.4 | 0:0:47:16 |
| 3 | 1 | 21a (1) | 5.5 | 0:0:47:22 |
| 4 | 2 | 21a (2) | 5.5 | nd:0:67:7 |
| 5 | 2 | 21 (2) | 5.5 | 35:0:60:4 |

The structures of compounds 25a and 26a were confirmed by X-Ray crystallography

Compounds 25a and 25b were then converted to the protected oxime 26 (Scheme 6) by reaction with trityl chloride, hydrolyzed and coupled with cystamine via activation as the N-succinimidyl ester (Nicolaou, K. C. et al., Chem.-Eur. J. 2001, 7, 4280-4295). Cleavage of the trityl protective group then gave 29a and 29b in 43% and 50% yield over the 4 steps from 25.

Scheme 7

Scheme 7

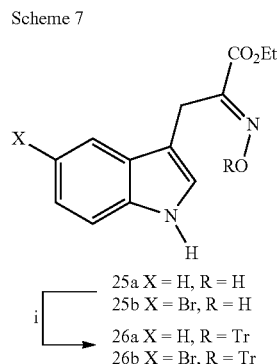

25a X = H, R = H
25b X = Br, R = H

26a X = H, R = Tr
26b X = Br, R = Tr

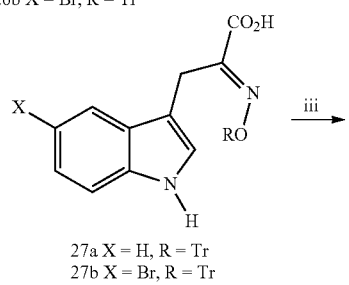

27a X = H, R = Tr
27b X = Br, R = Tr

-continued

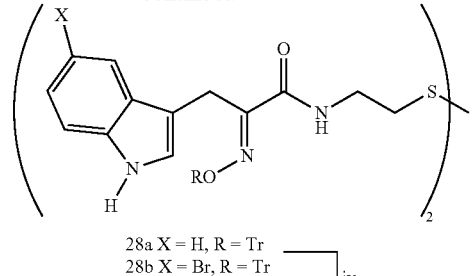

28a X = H, R = Tr
28b X = Br, R = Tr
29a X = H, R = H
29b X = Br, R = H

Reagents and conditions: (i) K₂CO₃, CH₂Cl₂, TrCl, 25° C., 20 h (97%, 26a; 74%, 26b). (ii) LiOH•H₂O, THF:H₂O (1:1), 25° C., 20 h (90%, 27a; 99%, 27b). (iii) i. EDC, NHS, dioxane, 25° C., 2 h. ii. Cystamine, Et₃N, MeOH, dioxane, 25° C., 15 h (64%, 28a; 84%, 28b). (iv) 2M HCl in Et₂O, CH₂Cl₂, 25° C., 2 h (78%, 29a; 81%, 29b).

The protection with a bulky group did not change the geometry E of the oxime 27 as confirmed by the X Ray structure.

Analogues with different chain lengths were synthesized in the same manner through coupling with the series of diamines (Scheme 8).

Scheme 8

Scheme 8

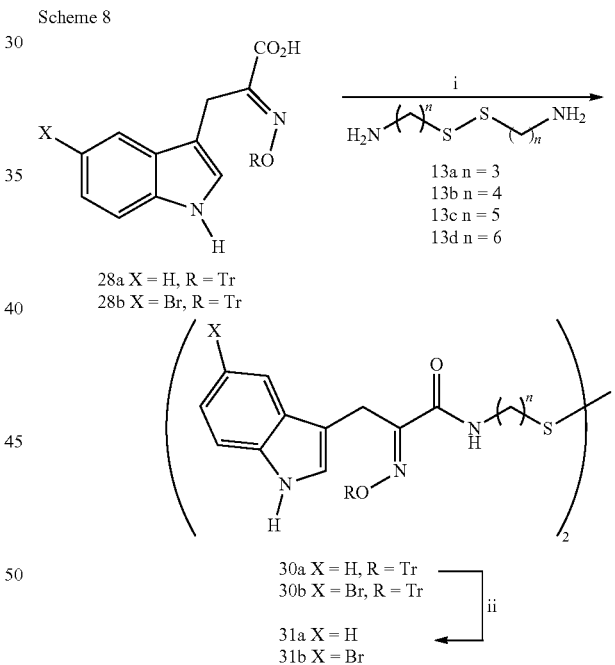

13a n = 3
13b n = 4
13c n = 5
13d n = 6

28a X = H, R = Tr
28b X = Br, R = Tr

30a X = H, R = Tr
30b X = Br, R = Tr
31a X = H
31b X = Br

Reagents and conditions: (i) i. EDC, NHS, dioxane, 25° C., 2 h. ii. 13, Et₃N, MeOH, dioxane, 25° C., 15 h. (iv) 2M HCl in Et₂O, CH₂Cl₂, 25° C., 2 h. The yields for each step are collected in the following Table 2:

TABLE 2

| Compound X = H | Yield 30a (%) | Yield 31a (%) | Compound X = Br | Yield 30b (%) | Yield 31b (%) |
|---|---|---|---|---|---|
| n = 3 | 54 | 70 | n = 3 | 34 | 50 |
| n = 4 | — | — | n = 4 | 25 | 70 |
| n = 5 | 41 | — | n = 5 | 21 | 96 |
| n = 6 | 38 | 70 | n = 6 | — | — |

This methodology was also exploited for the preparation of the entire series of bromoindol isomers. These bromoindoles were synthesized by application of the Leimgruber-Batcho methodology (Moyer, M. P. et al., H. *J. Org. Chem.* 1986, 56, 5106-5110) or by the Bartoli procedure (Nicolaou, K. C. et al., *J. Am. Chem. Soc.* 2004, 126, 12888-12896). Following the same steps indicated above, the series of psammaplin analogs built around the bromoindole regioisomers was obtained (Scheme 9).

Scheme 9

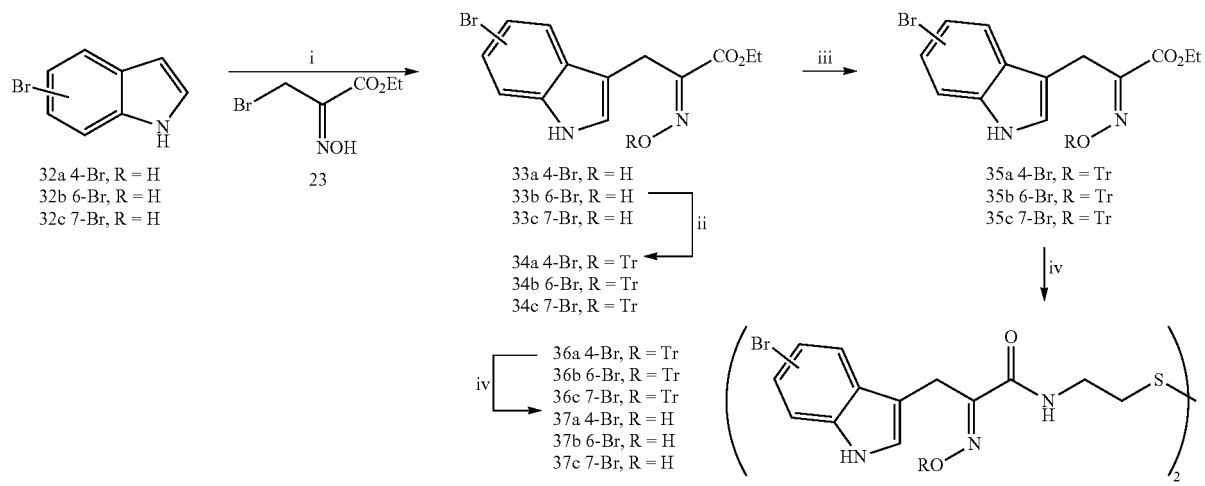

Reagents and conditions: (i) 23, K$_2$CO$_3$, CH$_2$Cl$_2$, 25° C., 20 h (65%, 33a; 43%, 33b, 41%, 33c). (ii) K$_2$CO$_3$, CH$_2$Cl$_2$, TrCl, 25° C., 20 h (74%, 34a; 51%, 34b, 41%, 34c). (iii) LiOH•H$_2$O, THF:H$_2$O (1:1), 25° C., 20 h (82%, 35a; 97%, 35b; 91%, 35c). (iv) i. EDC, NHS, dioxane, 25° C., 2 h. ii Cystamine, Et$_3$N, MeOH, dioxane, 25° C., 15 h (67%, 36a; 77%, 36b, 50%, 36c) (v) 2M HCl in Et$_2$O, CH$_2$Cl$_2$, 25° C., 2 h (81%, 37a; 54%, 37b; 60%, 37c).

Analogously, other compounds were synthesized by coupling acid 28b with amines 38 and 41 (Scheme 10). It was necessary to use TFA for the cleavage of the trityl group in 39 (Glinka, T. et al., *Bioorg. Med. Chem.* 2003, 11, 591-600).

Scheme 10

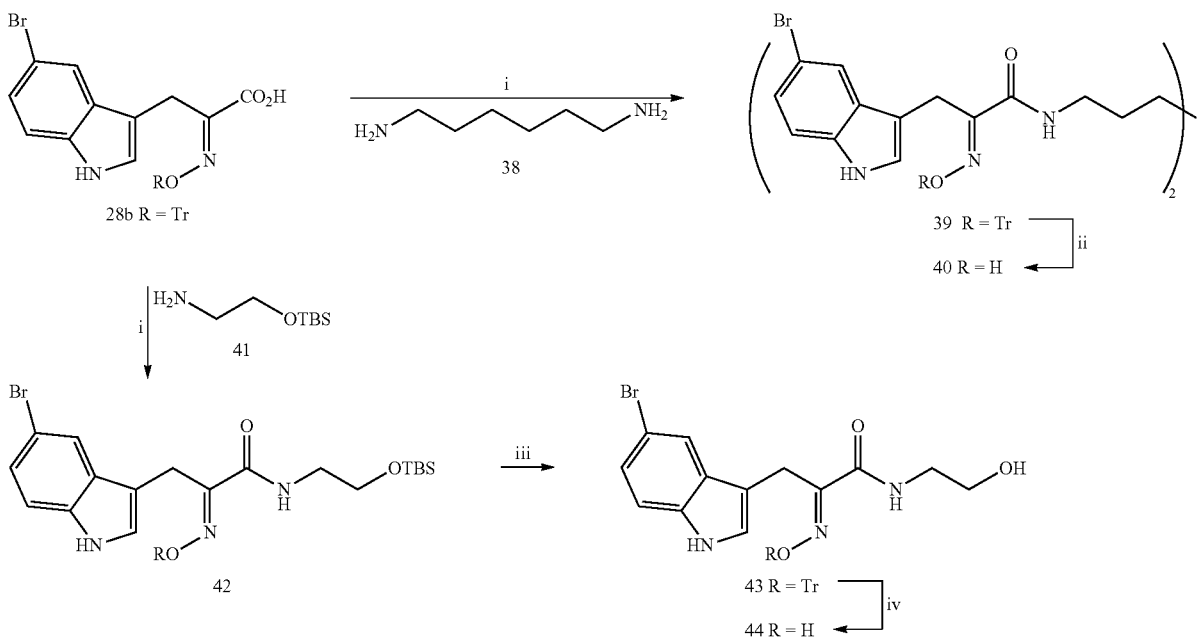

Reagents and conditions: (i) i. EDC, NHS, dioxane, 25° C., 2 h. ii. 38 or 41, Et$_3$N, MeOH, dioxane, 25° C., 15 h (74%, 39; 63%, 42). (ii) TFA, CH$_2$Cl$_2$, 0° C. to 25° C., 1 h (50%). (iii) THF:HCO$_2$H:H$_2$O (7:2:1), 19 h, 25° C. (99%). (iv) 2M HCl in Et$_2$O, CH$_2$Cl$_2$, 25° C., 2 h (59%).

Other compounds synthesized were the benzyl protected oxime (Rutger, R. P. et al., *J. Chem. Soc. Perkin Trans I* 1987, 2473-2480) (Scheme 11) and the methyl sulphide by reduction of the disulphide with NaBH$_4$ and methylation with MeI (Scheme 12) (Rutger, R. P. et al., *J. Chem. Soc. Perkin Trans I* 1987, 2473-2480).

Scheme 11

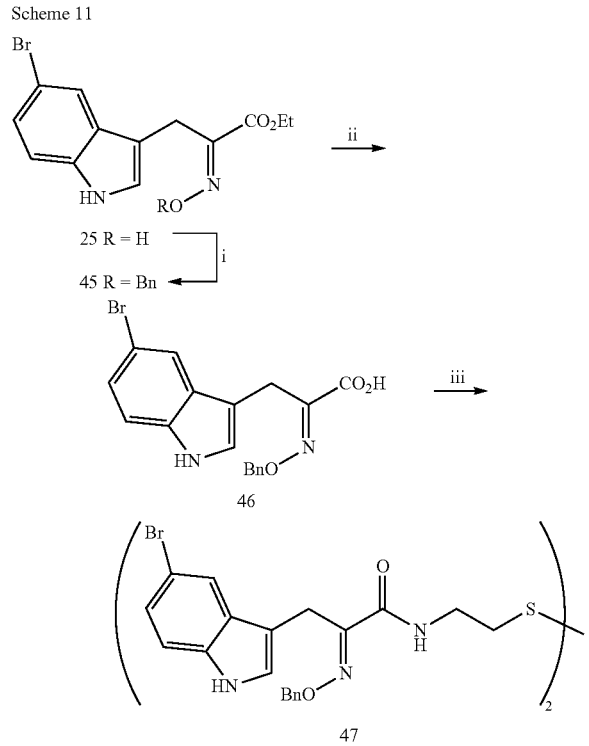

Reagents and conditions: (i) BnBr, KO$^t$Bu, DME, 12 h, 25° C. (72%). (ii) LiOH•H$_2$O, THF:H$_2$O (1:1), 25° C., 20 h (99%). (iv) i. EDC, NHS, dioxane, 25° C., 2 h. ii. Cystamine, Et$_3$N, MeOH, dioxane, 25° C., 15 h (80%).

Scheme 12

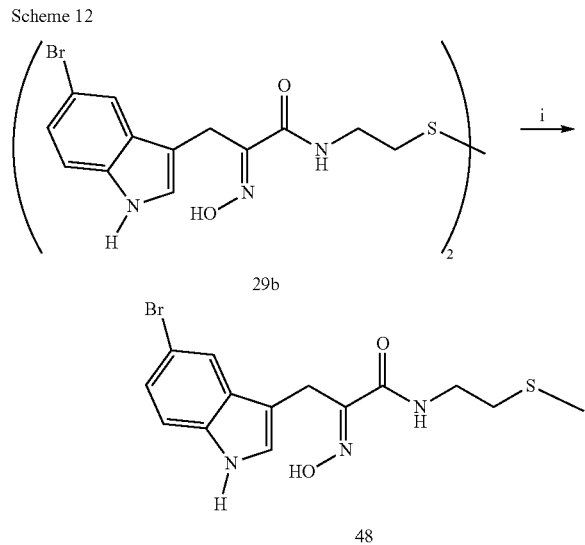

Reagents and conditions: (i) i. NaBH, NaOH, EtOH, 25° C., 0.5 h. ii. MeI, 25° C., 16 h, 25° C. (80%).

III—Biological Activity

A—Methods:

Cell Culture:

Human leukemia cell line U937 was propagated in RPMI medium supplemented with 10% FBS (Foetal bovine serum; Hyclone) and antibiotics (100 U/mL penicillin, 100 µg/mL streptomycin and 250 ng/mL amphotericin-B). Cells were kept at the constant concentration of 200000 cells per milliliter of culture medium. For AML samples, bone marrow containing 80% to 90% leukemic blasts was purified over Ficoll. This study was approved by the Ethical Committee of the Second University of Naples.

Ligands and Materials:

SAHA (Alexis) was dissolved in DMSO and used at $5\times10^{-6}$M. MS-275 (Schering A G) was dissolved in ethanol and used at $5\times10^{-6}$M; valproic acid (VPA; Sigma) was used at 1 mM. All other compounds described were dissolved in DMSO (Sigma-Aldrich) and used at 1 or 5 µM.

Cell Cycle Analysis:

$2.5\times10^5$ cells were collected and resuspended in 500 µL of a hypotonic buffer (0.1% Triton X-100, 0.1% sodium citrate, 50 µg/mL propidium iodide, RNAse A). Cells were incubated in the dark for 30 min. Samples were acquired on a FACS-Calibur flow cytometer using the Cell Quest software (Becton Dickinson) and analysed with standard procedures using the Cell Quest software (Becton Dickinson) and the ModFit LT version 3 Software (Verity). All the experiments were performed 3 times.

FACS Analysis of Apoptosis:

Apoptosis was measured with the caspase 3 activity detection (B-Bridge) as suggested by the suppliers and quantified by FACS (Becton Dickinson).

Granulocytic Differentiation:

Granulocytic differentiation was carried out as follows. Briefly, U937 cells were harvested and resuspended in 10 µL phycoerythrine-conjugated CD11c (CD11c-PE). Control samples were incubated with 10 µL PE conjugated mouse IgG1, incubated for 30 min at 4° C. in the dark, washed in PBS and resuspended in 500 µL PBS containing propidium iodide (0.25 µg/mL). Samples were analysed by FACS with Cell Quest technology (Becton Dickinson). Propidium iodide (PI) positive cells have been excluded from the analysis.

Western Blot Analyses:

Western Blot analyses were performed according to standard procedures following suggestions of antibodies suppliers. For the determination of p21$^{WAF1/CIP1}$ and p16$^{INK4}$ 100 µg of total protein extracts were separated on a 15% polyacrylammide gels and blotted. Western blots were shown for p21 (Transduction Laboratories, dilution 1:500), p16 (Santa Cruz) and total ERKs (Santa Cruz) were used to normalise for equal loading. For alpha-tubulin acetylation 25 µg of total protein extracts were separated on a 10% polyacrylamide gels and blotted. Western blots were shown for acetylated alpha-tubulin (Sigma, dilution 1:500) and total ERKs (Santa Cruz) or total tubulin (Sigma) were used to normalise for equal loading.

Isolation of Genomic DNA:

Cells were resuspended into 150 µl of TE (Tris 10 mM—EDTA 1 mM). 1.5 mL of lysis buffer (10 mM Tris pH 8.0—0.1 mM EDTA pH 8.0—0.5% SDS—20 µg/ml Rnase Dnase-free) were added, and after an incubation time of 1 h at 37° C., a second incubation at 56° C. with proteinase K at 100 μg/ml final concentration was performed over night. Proteins were removed by phenol-chloroform extraction. The genomic DNA was then precipitated with 0.2 vol. of 10M ammonium acetate and 2 vol. ethanol, and centrifuged at 13000 rpm for 5 min. The DNA pellet was washed with 70% ethanol, air dried and resuspended in nuclease free water at 4° C. on rocking table. The concentration was measured at 260 nm.

Digestion of Genomic DNA:

40 μg of genomic DNA were digested with 50 U EcoRV and PvuII (do not cut in the RARβ2 promoter) over night at 37° C. The proteins were removed by phenol-chloroform extraction, and the DNA was precipitated and resuspended with 40 μl filtered water.

In vitro Methylation of Genomic DNA:

20 μg of digested DNA were methylated with 8 U of Sss1 methylase (New England Biolabs) in presence of SAM 3.2 mM final concentration during 2 hrs at 37° C. After phenol-chloroforme extraction, the DNA is precipitated and resuspended with 20 μl filtered water.

Bisulfite Treatment and PCR for RARβ Methylation:

20 μg of genomic DNA (or in vitro methylated DNA) were mixed with 5.5 μl of 3M NaOH, the volume was adjusted to 55.5 μl with filtered water. After 15 min incubation at 42° C., 500 μl of 3M sodium bisulphite solution containing 0.05M hydroquinone were added. The mixture was incubated at 54° C. for 16 h. The modified DNA was purified with Nucleospin extract purification kit and eluted in 50 μl of filtered water. The eluate was desulphonated with 5.5 μl of 3M NaOH for 15 min at room temperature. 16.8 μl of 10M ammonium acetate, 1 μl glycoblue and 200 μl ethanol were added for the DNA precipitation. The DNA was recovered after centrifugation, washed, air dried and resuspended with 50 μl of filtered water. PCR was performed as follows: 5 min for denaturation at 94° C.; 35 cycles; 1 min. denaturation at 94° C., 1 min. annealing at 57.5° C. for the methylated primer and 52° C. for the unmethylated primer, 1 min. elongation at 72° C. 5 min further elongation at 72° C. The PCR product (10 μl+5 μl loading dye) was analyzed on 1.5% agarose gel.

```
RARβ2 methylated primer S:
5' TCG AGA ACG CGA GCG ATT CG;

AS:
5' GAC CAA TCC AAC CGA AAC GA;

RARβ2 unmethylated primer S:
5'TTG AGA ATG TGA GTG ATT TG;

AS:
5' AAC CAA TCC AAC CAA AAC AA
```

Bisulphite Treatment and PCR for p16 Methylation:

DNA extraction was performed as described below. Bisulfite treatment and PCR for the determination of p16 methylation was performed as described from the suppliers (Chemicon).

MTT Cytotoxicity Assay

HCT-116, A-375 and DU-145 cells were plated at 8000 cells per well in 96-well transparent cell culture grade plates (Corning). Plates were kept in the humidified $CO_2$ (5%) incubator overnight so that cells get attached to the bottom. Next morning compounds (SAHA, MS-275 and UVI 5008) were added at the concentrations of 100, 300, 1000, 3000 and 10000 nM and plates were again kept in the 5% $CO_2$ incubator for 48 h. After the complete 48 hrs treatment medium containing compounds were removed from each well. 0.5 mg/mL MTT (Sigma) was dissolved in medium and added to each well and the plates were incubated for 2 hrs. Viable cells cleave the MTT tetrazolium ring into a dark blue formazan reaction product, whereas dead cells remain colorless. The MTT-containing medium was gently removed and DMSO was added in each well. After shaking, the plates were read in absorbance at 540 nm. All results are expressed as the average of three wells. Percent cytotoxicity was measured of each compound and represented in terms of its $IC_{50}$ values.

Fluorescence-Activated Cell Sorter (FACS) Analysis by Anti-APO2.7 Monoclonal Antibody Induction of TC apoptosis was analyzed by APO2.7 (7A6) expression, which reacts preferentially with a 38 kDa mitochondrial membrane protein in cells undergoing apoptosis and was established by tracking cell viability and apoptotic response (Koester, S. K. et al., Cytometry 29, 306-12, 1997; Zhang, C., Ao, Z., Seth, A. & Schlossman, S. F., J Immunol 157, 3980-7, 1996). A375, DU145, HCT116 and MaTu cell lines were incubated with SAHA (1, 3, 10 μM), MS275 (1, 3, 10 μM) or UVI5008 (1, 3, 10 μM) for 48 h. After trypsinization, the cells with or without treatment were washed once in PBS. The cells were then incubated with PBS containing 2.5% FCS and 100 μg/ml digitonin at 4° C. After washing, the cells were incubated with mouse antihuman APO2.7 phycoerythrin-conjugated mAb (Beckman Coulter). The cells were washed and resuspended in PBS/2.5% FCS and analyzed by FACSort (Becton Dickinson). The labeled cells were analyzed for APO2.7 expression using CellQuest software (Becton Dickinson Immunocytometry Systems).

In vivo Anti-Tumor Activity of UVI 5008:

We have checked the anti tumor activity of this compound in vivo by xenografting HCT-116 colon carcinoma cells in immunoincompetent mice.

Materials and Method:

SAHA, a pan HDAC inhibitor was a gift of Merck, MS-275, a class I HDAC inhibitor was a gift of Schering and UVI 5008 was synthesized as disclosed above. All mice in the in vivo studies were athymic female nude Crl: Nu (Ico)-Foxn1nu mice (swiss) purchased from Charles River.

Preparation of Doses:

All the compounds were dissolved in 8% DMSO+2.5% Tween 80+89.5% Oil. Along with these three doses we have taken the vehicle control also.

Experimental Design:

$4 \times 10^6$ HCT-116 colon carcinoma cells were injected subcutaneously to the left flank of each animal. When the tumours were grown to 4 mm size, animals were randomised in the respective 4 groups, so that each group contains animals of approximately same size of tumours before treatment. Drugs were given through the intra-peritoneal route. Earlier tests revealed that SAHA at the dose of 30 mg/kg of mice was not tolerable to the mice and 60% mortality was observed. Therefore, the comparative study was carried out by reducing the dose to 20 mg/kg. UVI 5008 at 30 mg/kg was well tolerated and no mortality was observed in earlier studies; the dose was therefore increased to 40 mg/kg and MS-275 was given at the dose of 20 mg/kg as SAHA. The treatment was given every second day. There were 10 animals in each group. Tumour size was determined using Vernier Calliper measurement. The tumour volume was determined by using the formula: TV=(a2×b)/2 (in which a represents width and b the length of the tumour).

Activity of the UVI5008 on Human SIRT1 and 2:

The SIRT activity assay was performed using the human recombinant SIRT1 and SIRT2. SIRT1 (1 U/well) or SIRT2 (5 U/well), respectively, were incubated (37° C. for 1 h) with the SIRT1/2 substrate (corresponding to a p53 acetylated peptide) in the presence of $NAD^+$ and various concentrations of tested compounds (sirtuins activators or inhibitors). Activity was measured as fluorescence intensity. As internal controls, sodium suramin, a sirtuin inhibitor, and resveratrol, a SIRT1 activator, have been included. The fluorescence was measured on a fluorometric reader (Inphinite 200 TECAN) with excitation set at 360 nm and emission detection set at 460 nm Activity of the UVI5008 on p53 Acetylation:

MCF7 cells (human breast cancer cells) have been growth following standard procedure and have been treated for 6 hrs with the indicated compounds in presence of 25 µM Etoposide. Total protein extracts have been run on SDS gel and blotted. Western Blot has been carried out by using the anti p53 ac382 (Abcam) following standard procedures. ERKs (Santa Cruz) have been used for equal loading control.

Study of Post-Translational Modifications on Histone Proteins Upon Treatment of the Cells with the UVI5008:

U937 cells were grown in RPMI medium in the presence of lysine and arginine ('light') or istope versions, Arg10 and Lys8 ('heavy'). Cell grown in light medium were treated for 24 h with UVI5008 or SAHA at 5 µM final concentration. As controls, cell grown in heavy medium were treated for 24 h with DMSO. Light and heavy cells were $7.5 \times 10^6$ cells harvest and mixed in 1:1 ratio (total $15 \times 10^6$ cells). The cells were washed twice with PBS and the cell pellet was stored at −80° C.

Histone Extraction

Cells were resuspended in 750 µl Triton Extraction Buffer (TEB: PBS containing 0.5% Triton X 100 (v/v), 2 mM phenylmethylsulfonyl fluoride (PMSF) and 0.02% (w/v) $NaN_3$) and lysed on ice for 10 min with gentle stirring. The lysate was centrifuged for 10 min at 6000 rpm and the supernatant discarded. The pellet was washed with 375 µl of TEB and peletted by centrifugation as before. Pellet is resuspended in 20 µl 250 mM HCl and acid extraction of the histones was performed o/n at 4° C.

Mass Spectrometry

Extracted histones were cleared by centrifugation and separated on a 15% acrylamide gel and the gel was stained with Coomassie. The gel region containing the histones was sliced, reduced and alkylated in gel. Proteins were digested o/n with trypsin (Promega). Peptides were eluted from the gel with trifluoroacetic acid. 8 µl out of total 20 µl were sequenced using nano-high-pressure liquid chromatography Aligent 1100 nanoflow system connected online to a 7-Tesla linear quadrople ion-trap Fourier transform (FT) mass spectrometer (Thermo Electron, Bremen, Germany). The peptides were eluted from the C18 column by applying a 30 minutes gradient, whereby buffer B increases from 3% to 40% with a flow of 30 µl/min. The Mascot algorithm was used to identify the peptides/proteins.

Mascot Search Criteria:
MS/MS Ion Search
Enzyme: Trypsin
Fixed modifications: Carbamidomethyl (C)
Variable modifications: Acetyl (K), Arg heavy 6C13 4N154 (R), di-Methylation (K), di-Methylation (R), GlyGly (ubiquitination) (K), Lys +8 6C13 2N15 (K), Methyl (K), Methyl (R), Oxidation (M)
Mass values: Monoisotopic
Protein Mass: Unrestricted
Peptide Mass Tolerance: ±10 ppm
Fragment Mass Tolerance: ±0.8 Da
Max Missed Cleavages: 3
Instrument type: ESI-TRAP U937 cells were treated with UVI5008 for 24 hrs and histones were acid extracted. Proteins were digested with trypsin and the peptides were analysed using a nanoLC that is online with a FT-ICR mass spectrometer. Peptides were identified on the basis of their parental ion mass and that of the fragmentation patterns using Mascot. The masses of the b- or y-ions are listed in the table (FIG. 10b). Masses indicated in bold character fit with high mass accuracy to the predicted fragments of the YQKSTELLIP peptide.

Western Blot Analysis:

The analysis was performed using an antibody that specifically recognizes K56 acetylated. A). Equal amounts of histones extracted from U937 cells (lanes 1 and 3 on FIG. 12A) and U2OS cells (lanes 2 and 4 on FIG. 12A) treated with solvent DMSO (lanes 1 and 2) or with UVI 5008 (lanes 3 and 4) for 24 hrs were loaded on a SDS gel. The arrowhead indicates the position of histone H3. B). The treatment of U937 cells with solvent (− on FIG. 12B) or with UVI 5008 (+ on FIG. 12B) for 5 minutes, 30 minutes or 1, 2, 3 or 4 hrs. The same blot was developed with a histone H3 core antibody, stripped and re-probed with the H3K56 acetylated specific antibody.

B—Results:

MTT Cytotoxicity Assay:

Percent cytotoxicity is represented in terms of its $IC_{50}$ values in table 3 here-under.

TABLE 3

$IC_{50}$ values of SAHA, MS-275 and UVI5008 in three different cancer cell lines using MTT cytotoxicity assay
$IC_{50}$ values in µM

|  | SAHA | MS-275 | UVI 5008 |
| --- | --- | --- | --- |
| A-375 | 3.1 ± 0.7 | 2.4 ± 0.7 | 3.1 ± 0.5 |
| HCT-116 | 3.1 ± 0.5 | 2.3 ± 0.3 | 1.8 ± 0.1 |
| DU-145 | 3.2 ± 0.5 | 8.2 ± 0.6 | 2.4 ± 0.3 |

Induction of Cell Cycle Arrest and Apoptosis:

Psammaplin A (UVI5000) and derivatives (UVI5004, UVI5008, UVI5010) thereof (FIG. 7) induced inhibition of proliferation (FIG. 1a) and/or apoptosis (FIG. 1b) in U937 acute myeloid leukemia cell line (FIG. 1). These compounds induced a cell cycle arrest which ranged from blocks in the G1 (UVI5010 at 1 µM) to arrests in the S and G2 phases (UVI5000, UVI 5004, UVI5008). Notably, there is a characteristic dose-dependent switch in the position of the block within the cell cycle for some compounds, such as UVI5010, which blocks in G1 at 1 µM and arrests cells in G2-M at 5 µM (FIG. 1a). UVI5008 is particular in that it arrests cells in G2-M already at 1 µM. These data suggest that these UVI compounds affect several checkpoints of the cell cycle with distinct efficacies. In line with the cell cycle effects the expression of the cell cycle inhibitors p21$^{WAF1/CIP1}$, known to be required for G1 and sustained G2 arrests (Bunz, F. et al., Science 282, 1497-501 (1998)), is dramatically increased as shown for UVI5000, UVI5008 and UVI5010 (FIG. 1c).

In addition to affecting cell cycle progression the UVI compounds induced apoptosis, albeit to a very different extent. Interestingly, those compounds that have the most pronounced effect on the G2-M arrest exert also the strongest apoptogenic effect (UVI5000, UVI5008, UVI5010 in FIG. 1b).

The anti-proliferative and apoptogenic action of psammaplin A and its two derivatives 5008 and 5010 was confirmed also in solid cancer cell line such as breast cancer cells (ZR75.1) and prostate cancer cells (LnCap; data not shown; see also FIG. 6).

UVI5008 is a Powerful HDAC Inhibitor:

Psammaplin A (UVI5000) is known as a weak histone deacetylase inhibitor and exposure of U937 cells to UVI5000 led to a moderate time-dependent increase of histone H3 acetylation (FIG. 1d, lanes 2, 3). This activity is dramatically enhanced with UVI5008 (FIG. 1d, lanes 4, 5), while UVI5010 does not significantly affect global H3 acetylation (FIG. 1d, lanes 6, 7). Specific histone acetylation is affected similarly as global H3 acetylation, as H3K9, H3K14 and H3K18 acetylations are all increased in presence of UVI5008 (FIG. 1e, lanes 4, 5) and to a lesser extent by the parental compound UVI5000 (FIG. 1e, lanes 2, 3). Interestingly, even though UVI5010 does not measurably affect global histone H3 acetylation, this compounds does act as HDAC inhibitor, as it enhances H3K18 and to a lesser extent H3K14 acetylation (FIG. 1e, lanes 6, 7).

Methylation of H3K9 is inversely correlated with acetylation, which is generally considered a "transcription activating" modification at promoters while methylation is a "silencing" modification. In keeping with this, methylation of H3K9 was decreased by exposure to UVI5008 (FIG. 1d middle panel; compare lane 1 with lanes 4 and 5).

UVI5008 and its parent compound UVI5000 displayed HDAC inhibitor activity in in vitro assays as well. Indeed, while UVI5000 is only a weak inhibitor of HDAC1, UVI5008 blocks HDAC1 activity nearly quantitatively and most notably more efficiently than the established class I—selective HDAC inhibitor MS275 (FIG. 1f) which is currently entering phase II clinical trials. Moreover, also the deacetylase activity HDAC4, a member of the class II HDACs, is nearly completely blocked by UVI5008 while UVI5000 displays only moderate activity (FIG. 1g). In keeping with this observation UVI5008 (as well as UVI5000 and UVI5010) inhibited the activity of HDAC6, another class II HDAC whose substrate is alpha tubulin (FIG. 1c, middle panel, compare lane 1 with lanes 2-7; note the amount of total alpha tubulin in the panel below for comparison). Together these data reveal that UVI5008 acts as a pan-HDAC inhibitor which blocks both class I and class II HDAC activities. Importantly, UVI5008 is more active in this assay than SAHA (vorinostat, Zolinza®), which has been approved for the treatment of cutaneous T-cell lymphoma and is in clinical trials for other indications.

UVI5008 Inhibits DNA Methylation in the Promoter Region of the Tumour Suppressor Genes p16$^{INK4a}$ and RARβ2:

To study if UVI5008 would have additional activities the possible inhibition of the DNA methylation of the promoters of tumor suppressor genes was studied. The promoter of RARβ2 is known to be silenced by methylation of CpG islands in its promoter. Using methylation-specific PCR (MSP) a significant increase of unmethylated RARβ2 was observed with UVI5008 (FIG. 2a). Similarly, MSP revealed a decrease of CpG island methylation at the p16$^{INK4a}$ promoter, another well established tumor suppressor gene and cell cycle regulator. Concomitantly, the amount of unmethylated p16$^{INK4a}$ promoter DNA increased by treating with UVI5008 (FIG. 2b). In this case, also UVI5000 displayed a similar activity. Notably, the classical DNA methyltransferase inhibitor 5-azacytidine ("AZA") showed an activity that was very similar to that seen with UVI5008, while SAHA was inactive (FIG. 2b). In keeping with the demethylation of the p16$^{INK4a}$ promoter the p16$^{INK4a}$ gene expression was de-silenced by exposure to UVI 5008, to a lesser extent also by UVI5000 and UVI5010, and this expression was comparable to that seen with the combination of 5-deazacytidine with SAHA (FIG. 2c).

Finally, using in vitro DNA methyltransferase (DNMT) assays it was confirmed that UVI5008 is a DNMT inhibitor which is nearly as active as RG108 albeit at higher concentrations (FIG. 2d).

UVI5008 Alters the Acetylation Status of Chromatin at the TRAIL Locus which Encodes a Tumor-Selective Apoptosis Inducing Death Ligand:

Our previous work has revealed that HDAC inhibitors such as MS275 induces expression of the TNF-related apoptosis inducing ligand TRAIL (also termed Apo2L or TNFSF10) in hematopoietic cell lines and patients blasts (Insinga, A. et al., Nat Med 11, 71-6 (2005); Nebbioso, A. et al., Nat Med 11, 77-84 (2005)). Notably, UVI5008 exposure of U937 myeloid cells leads to a rapid dramatic H3K9 acetylation of the chromatin at the TRAIL promoter and with a delayed kinetics also at the first intron (FIG. 5a). This "activating" chromatin mark correlates with increased expression both at the mRNA (FIG. 5b) and protein (FIG. 5b) levels, as shown by RT-PCR and ELISA assays, respectively.

Structure-Activity-Relationship (SAR) Studies of HDAC Activity:

To initiate a SAR study of the above described HDAC inhibitor activities of UVI5008 a series of derivatives was synthesized (Table 1). The activity readouts that were systematically investigated were cell cycle arrest and p21$^{WAF1/CIP1}$ induction, induction of differentiation and acetylation of targets (in this case a-tubulin). The aim was to understand the role of particular structural elements and particular substitutions, in particular whether (i) one or both units of the symmetrical molecules are necessary for biological activity, (ii) the disulphide bridge is dispensable or not, and (iii) finally whether an uncleavable compound would display any action.

Position of bromine substitution: UVI5008 has Br attached to C5 of the indole ring. Changing the substitution from C5 to C6 (UVI5013) had only a minor effect on cell cycle arrest and apoptosis (FIG. 3a), and rather increased the induction of differentiation measured by expression of the CD11c marker (FIG. 3b). As expected p21$^{WAF1/CIP1}$ was similarly induced as for UVI5008, while the inhibition of HDAC6, as measured by acetylation of alpha tubulin, was somewhat reduced (FIG. 3c lane 9). Substitution of Br at C7 (UVI5014) reduced weakly the cell cycle arrest and apoptosis but the levels of p21$^{WAF1/CIP1}$ induction and alpha tubulin acetylation were very similar to that seen with UVI5008 (FIGS. 3a, b; FIG. 3c lane 12). The placement of the bromine atom at C4 considerably reduced the activity (UVI 5012).

Oxime: The oxime function is required for activity, as the triphenyl methyl (trityl) (UVI5018) and benzyl (UVI5017) derivatives are inactive in all the assays shown in FIGS. 3a, b and FIG. 3c (lanes 13, 14).

Disulphide bridge: The presence of a disulphide bridge is essential for activity, as replacement of the sulphur by carbon (UVI5019) results in an inactive molecule (FIGS. 3a, b and FIG. 3c lanes 15). The same hold true for a corresponding analogue of UVI5000 (Psammaplin A), as UVI5022, a S→C substitution product, is inactive in all assays displayed in FIGS. 3a, b and FIG. 3c (lane 18). Thus the presence of one or two sulphur atoms, and/or the disulphide bridge and/or the cleavage of the active UVI5000 and UVI5008 are required for cell cycle arrest, apoptosis induction and differentiation.

Monomeric homologues: UVI5008 and all active derivatives are dimeric cleavable molecules, which generate the corresponding thiols upon reduction. This thiol is necessary for activity, as the hydroxyl derivative UVI5021 is inactive (FIGS. 3a, b and FIG. 3c lanes 17). The same observation is made for UVI5023, the hydroxyl derivative of UVI5000 (FIGS. 3a, b and FIG. 3c lanes 19). Interestingly however, the methylthioester UVI5020 is inactive at inducing apoptosis and G2M arrest but it induces a G1 arrest and the corresponding enhanced expression of p21$^{WAF1/CIP1}$ (FIGS. 3a, b and FIG. 3c lanes 16).

Psammaplin A Derivatives Induce Apoptosis in AML Patient Blasts:

The intriguing anticancer potential of some psammaplin A derivatives prompted us to test their activity in ex vivo AML patient blasts. As shown in FIG. 4, both psammaplin A(UVI5000) and UVI5008 induced cell cycle arrest and apoptosis in the blasts, as measured by caspase 3 activation assays in 4 independent ex vivo cultures of different patients (AML patients #102, #108, #109, #116). It must be noted that well known HDACi's such as MS275 and SAHA displayed activities similar to UVI5008. To verify the action on ex vivo AML patient blasts of the secondarily made derivatives, we tested the activity of compounds UVI5008, UVI5013, UVI5014 and UVI5020 at the concentration of 5 µM. As shown in FIG. 4, all tested derivatives showed an apoptotic activity in two different samples of patient blasts. Note that UVI5020 showed only a weak induction of apoptosis in keeping with the above described altered activity profile.

Anti-proliferative activity on cancer cell lines A-375, DU145 and HCT-116:

Dose response curves with UVI5008 revealed potent antiproliferative activity on different types of cancer cell lines with IC$_{50}$ values ranging between 1.5 to 3 µM (FIG. 8a-c).

In vivo Anti-Tumor Activity of UVI 5008:

Results are illustrated in FIGS. 9A and 9B. All the compounds were used at their maximum tolerated doses. There was no mortality in any of the treatment groups. There were some signs of toxicity in UVI5008 treatment group in 3 animals out of 10 in the form of accumulation of intra peritoneal fluid due to which their weight was increased compared to other animals. No other toxicity symptoms were observed. We conclude from this experiment that UVI5008 was showing greater anti tumoral activity with respect to SAHA and MS-275 at their MTD and none of the compounds caused animal weight loss. Normalised tumor weight profile is given in table 4:

Percent Growth Inhibition are given in table 5 here-under:

TABLE 5

| Percent Growth Inhibition after 22 days | |
|---|---|
| SAHA 20 mg/kg | 21 ± 17 |
| MS-275 20 mg/kg | 35 ± 12 |
| UVI 5008 40 mg/kg | 56 ± 7 |

Study of Post-Translational Modifications on Histone Proteins Upon Treatment of the Cells with UVI5008:

An extensive Mass Spectrometric analysis was performed to identify post-translational modifications on histone proteins that were induced or removed upon treatment of the cells with the UVI5008. The high accuracy of the FT-ICR mass spectrometer allowed us to determine the various post-translational modifications of the histones including the unambiguous identification of acetylated peptides. Treatment of U937 (and other) cells with UVI5008 resulted in shift of the relative abundance of acetylated peptides (SILAC study) as well as in the identification of a novel acetylated lysine residue in histone H3, H3K56 (FIG. 10a). Hitherto, the acetylation of H3K56 was solely detected by us and other in lower eykaryotes [Ozdemir A, Spicuglia S, Lasonder E, Vermeulen M, Campsteijn C, Stunnenberg H G, Logie C., Characterization of lysine 56 of histone H3 as an acetylation site in *Saccharomyces cerevisiae*. J Biol Chem. 2005 Jul. 15; 280(28): 25949-52. Epub 2005 May 10] and reviewed in [Ozdemir A, Masumoto H, Fitzjohn P, Verreault A, Logie C. Histone H3 lysine 56 acetylation: a new twist in the chromosome cycle *Cell Cycle.* 2006 November; 5(22):2602-8. Epub 2006 Nov. 15]. Studies in yeast had revealed that this modification occurs in virtually all the newly synthesized histones that are deposited into chromatin during S-phase in yeast. Removal of K56 acetylation takes place in the G2/M phase of the cell cycle and is dependent upon Hst3 and Hst4, two proteins that are related to the NAD+-dependent histone deacetylase Sir2. On the basis of the yeast data, it was tested whether human Sir1 and/or -2 can be inhibited by UVI5008 in vitro and whether acetylation of a known Sir2 substrate, namely p53, was increased following UVI5008 treatment in vivo.

Activity of UVI5008 on Human SIRT1 and 2:

Results are illustrated in FIG. 13A. The activity of UVI5008 has been tested at 2 different concentrations on human SIRT1 and 2. As controls we have been using known activators and inhibitors such as resveratrol and suramin (A). As clearly shown UVI5008 showed inhibitory capacities against both. We have been calculating the IC50 of UVI5008 as 8.9 µM on SIRT1 and 7.8 µM on SIRT2. These data clearly demonstrate that UVI5008 is a good SIRT1 and SIRT2 inhibitor. Some of the anticancer activities might thereby also due to this action as reported for other SIRT inhibitors in cancer cells.

TABLE 4

| | Normalised tumour weight profile in mg (mean of n = 10) | | | | |
|---|---|---|---|---|---|
| Days | 1 | 4 | 12 | 17 | 22 |
| Vehical control | 100 ± 21.7 | 231.71 ± 80.7 | 1305.14 ± 321.7 | 2689.1 ± 578.2 | 3701.3 ± 695.5 |
| SAHA 20 mg/kg | 100 ± 24 | 166.69 ± 56.8 | 892.95 ± 267.6 | 1915.59 ± 409.5 | 2952.8 ± 636.4 |
| MS-275 20 mg/kg | 100 ± 25 | 202.6 ± 81.5 | 746.65 ± 185 | 1360.61 ± 288 | 2423.09 ± 445.5 |
| UVI 5008 40 mg/kg | 100 ± 21.5 | 180.55 ± 43 | 548.73 ± 109.8 | 915.28 ± 196.8 | 1684.79 ± 262.1 |

Activity of the UVI5008 on p53 Acetylation:

FIG. 13B illustrates the effects of UVI5008 on p53 acetylation levels, taken as readout of SIRT inhibition. This experiment has been performed in MCF7 cells which are p53 WT in co-treatment with Etoposide 25 μM to induce DNA alterations and activate p53. We could confirm the hyperacetylation action of UVI5008 on p53.

The invention claimed is:

1. A molecule of formula (I):

[Structure of Formula (I)]

wherein:
n is an integer selected from 1, 2, 3, 4, 5, 6, 7, and 8;
i is an integer selected from 1 and 2;
j is an integer selected from 0 and 1;
when i=2, then j=0 and when i=1, then j=1;
X is a halogen atom;
W is —CO—NH—;
R is selected from the group consisting of: a hydrogen atom, a $C_1$-$C_6$ alkyl group, a $C_1$-$C_6$ and a carboxyalkyl group;
$R_1$, $R_2$ and $R_3$ are independently selected from the group consisting of: a hydrogen atom, a $C_1$-$C_6$ alkyl group, a $C_1$-$C_6$ halogenoalkyl group, a halogen atom, a hydroxyl group, a $C_1$-$C_6$ alkoxy group, a $C_1$-$C_6$ aminoalkyl group, a $C_1$-$C_6$ saturated heterocycloalkyl group, a $C_6$-$C_{12}$ aryl group, a $C_6$-$C_{20}$ aralkyl group, and a $C_4$-$C_{12}$ heteroaryl group;
$R_4$ is selected from the group consisting of: a hydrogen atom, a $C_1$-$C_6$ alkyl group, a $C_2$-$C_6$ acyl group, a $C_6$-$C_{12}$ aryl group, a $C_6$-$C_{20}$ aralkyl group, and a $C_4$-$C_{12}$ heteroaryl group;
$R_5$ is selected from the group consisting of: a hydrogen atom, a $C_1$-$C_6$ alkyl group, and a $C_6$-$C_{20}$ aralkyl group;
and its pharmaceutically acceptable salts.

2. The molecule according to claim 1, wherein:
n is an integer selected from 2, 3, 4, 5, and 6;
i is 2;
j is 0;
X is Br;
$R_1$, $R_2$ and $R_3$ are hydrogen atoms;
$R_4$ is H; and
$R_5$ is H.

3. The molecule according claim 1, wherein the molecule is selected from the group consisting of:

UVI 5008

UVI 5009

UVI 5010

UVI 5011

UVI 50012

UVI 5013

UVI 5014

UVI 5020

4. A pharmaceutical composition comprising a molecule of formula (I) according to claim 1 or a salt thereof in a pharmaceutically acceptable carrier.

5. A pharmaceutical composition comprising a molecule of formula (I) according to claim 2 or a salt thereof in a pharmaceutically acceptable carrier.

6. A pharmaceutical composition comprising a molecule of formula (I) according to claim 3 or a salt thereof in a pharmaceutically acceptable carrier.

7. The pharmaceutical composition according to claim 4 wherein the pharmaceutically acceptable carrier is water.

8. The pharmaceutical composition according to claim 5 wherein the pharmaceutically acceptable carrier is water.

9. The pharmaceutical composition according to claim 6 wherein the pharmaceutically acceptable carrier is water.

10. A method for the synthesis of a molecule of formula (III), as an intermediate in the synthesis of a molecule of formula (I) according to claim 1, wherein the method comprises the step as depicted in Scheme 3:

Scheme 3

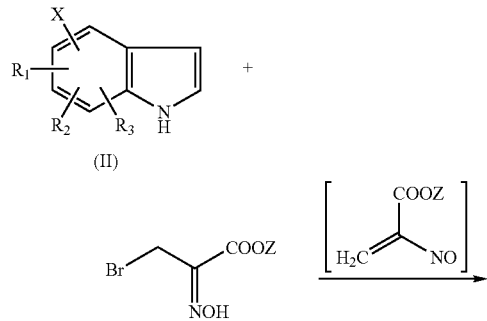

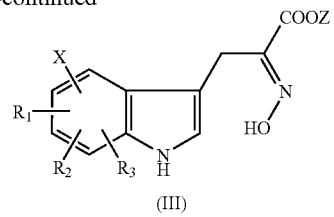

(III)

and wherein indole (II) is alkylated with nitrosoacrylate $CH_2=C(NO)-COOZ$ and Z is selected from the group consisting of $C_1$-$C_6$ alkyl, phenyl and aryl.

11. The method for the synthesis of a molecule of formula (III), according to claim 10, wherein the nitrosoacrylate $CH_2=C(NO)-COOZ$ is generated in situ from the corresponding bromo-oxime and the reaction is conducted in a basic medium, in a solvent, at ambient temperature.

12. The method for the synthesis of a molecule of formula (III) according to claim 11, wherein Z is an ethyl group, the solvent is $CH_2Cl_2$, and the base is $K_2CO_3$.

13. A method for the synthesis of a molecule of formula (I) according to claim 1, from a molecule of formula (III), wherein the method comprises the steps as depicted in Scheme 4:

Scheme 4

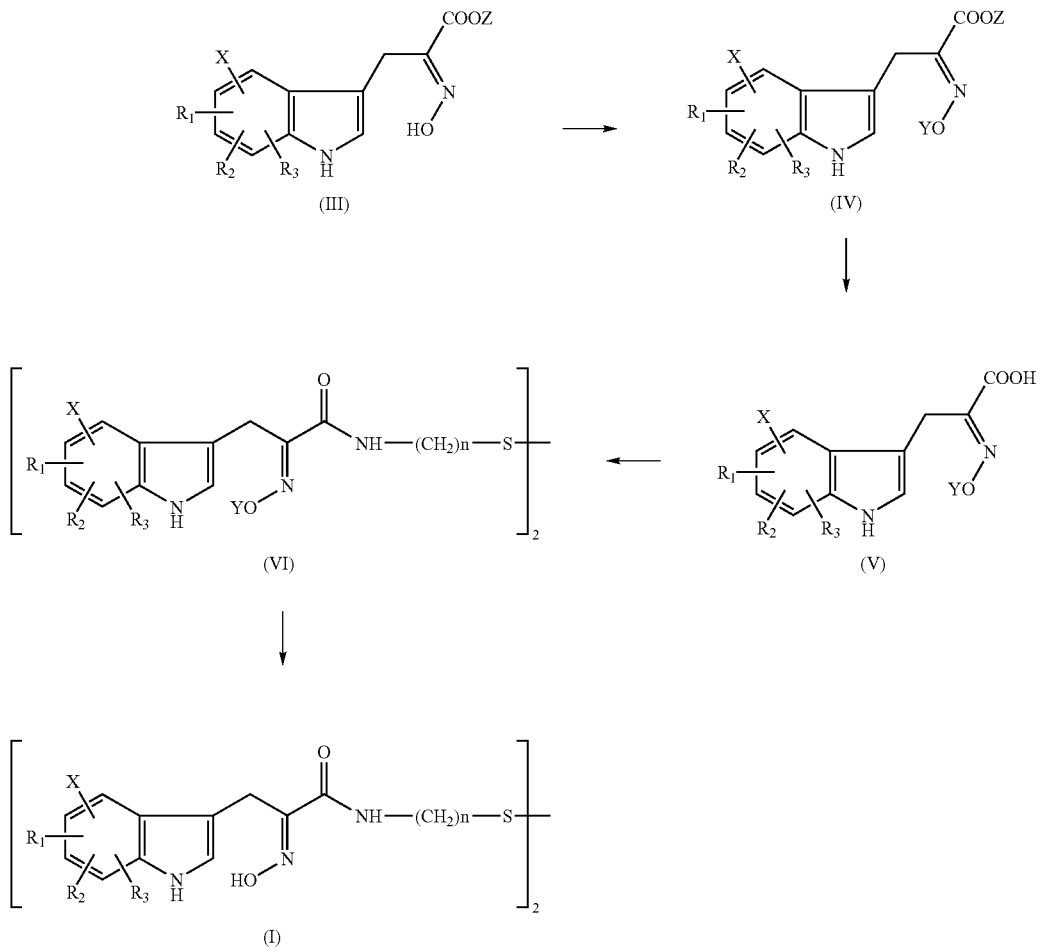

wherein $R_4$ and $R_5$ are H, i=2, j=0 and X, $R_1$, $R_2$ and $R_3$ have the values recited in claim 1;

wherein the oxime (III), where Z is selected from the group consisting of $C_1$-$C_6$ alkyl, phenyl and aryl, is converted to compound (IV) by protection of the oxime function with protective group Y selected from the group consisting of trityl, benzyl, methoxy methyl, methoxy ethoxy methyl and 2-tetrahydropyranyl trityl;

then the ester function —COOZ is deprotected to —COOH to give the molecule (V), and wherein molecule (V) is reacted with a di-amine $NH_2$—$(CH_2)_n$—S—S—$(CH_2)_n$—$NH_2$ to give (VI), and the oxime function is then liberated to produce the molecule of formula (I).

14. The method according to claim 13, wherein Y is a trityl group.

15. A method for the synthesis of a molecule of formula (I) according to claim 1, from a molecule of formula (V), wherein, the method comprises the steps as depicted in Scheme 5:

nyl trityl, is reacted with an amine $H_2N$—$(CH_2)_n$—S—R to give compound (VI) and the oxime function is deprotected to give the molecule of formula (I).

16. A method for treating cancer comprising administering to an individual in need thereof an effective amount of a molecule of formula (I) or salt thereof as claimed in claim 1, wherein said cancer is selected from the group consisting of: lung, ovarian, central nervous system (CNS), skin, colon cancer and leukemia.

17. A method for treating cancer comprising administering to an individual in need thereof an effective amount of a molecule of formula (I) or salt thereof as claimed in claim 3, molecule of formula (I) or salt thereof as claimed in claim 3,

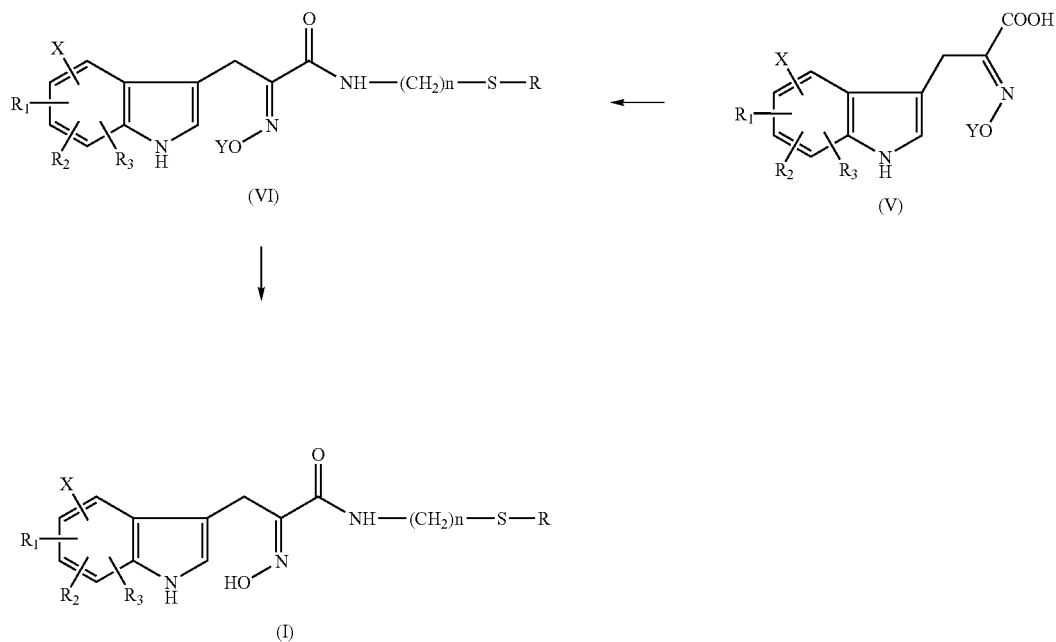

wherein $R_4$ and $R_5$ are H, i=1, j=1 and X, R, $R_1$, $R_2$ and $R_3$ have the values recited in claim 1;

wherein compound (V) with a protective group Y selected from the group consisting of trityl, benzyl, methoxy methyl, methoxy ethoxy methyl and 2-tetrahydropyrawherein said cancer is selected from the group consisting of: lung, ovarian, central nervous system (CNS) skin colon cancer and leukemia.

* * * * *